US012778641B2

(12) United States Patent
Jones James et al.

(10) Patent No.: US 12,778,641 B2
(45) Date of Patent: Nov. 3, 2026

(54) CERVICAL PLATE

(71) Applicant: MiRus LLC, Marietta, GA (US)

(72) Inventors: Kaitlin Jones James, Atlanta, GA (US); Noah Roth, Marietta, GA (US)

(73) Assignee: MiRus LLC, Marietta, GA (US)

( * ) Notice: Subject to any disclaimer, the term of this patent is extended or adjusted under 35 U.S.C. 154(b) by 279 days.

(21) Appl. No.: 18/153,794

(22) Filed: Jan. 12, 2023

(65) Prior Publication Data

US 2023/0225769 A1 Jul. 20, 2023

Related U.S. Application Data

(63) Continuation-in-part of application No. 29/823,883, filed on Jan. 20, 2022, now Pat. No. Des. 1,004,776.

(60) Provisional application No. 63/410,015, filed on Sep. 26, 2022, provisional application No. 63/359,335, filed on Jul. 8, 2022, provisional application No. 63/303,126, filed on Jan. 26, 2022.

(51) Int. Cl.
*A61B 17/70* (2006.01)
*A61B 17/00* (2006.01)

(52) U.S. Cl.
CPC .................... *A61B 17/7059* (2013.01); *A61B 2017/00367* (2013.01)

(58) Field of Classification Search
CPC . A61B 17/80; A61B 17/8033; A61B 17/8042; A61B 17/8061; A61B 17/7059
See application file for complete search history.

(56) References Cited

U.S. PATENT DOCUMENTS

| | | | | |
|---|---|---|---|---|
| 6,306,136 | B1 | 10/2001 | Baccelli | |
| 6,602,256 | B1 | 8/2003 | Hayes | |
| 6,602,257 | B1 | 8/2003 | Thramann | |
| 6,679,883 | B2 | 1/2004 | Hawkes et al. | |
| 7,066,961 | B2 | 6/2006 | Michelson | |
| 7,220,263 | B2 | 5/2007 | Cordaro | |
| 7,306,605 | B2 | 12/2007 | Ross | |
| 7,318,825 | B2 | 1/2008 | Butler et al. | |
| 7,815,666 | B2 | 10/2010 | Baynham et al. | |
| 8,328,854 | B2 | 12/2012 | Baynham et al. | |
| 8,778,001 | B2 | 7/2014 | Thramann et al. | |
| 8,961,517 | B2 | 2/2015 | McClintock et al. | |
| 9,149,311 | B2 | 10/2015 | Elsbury | |
| 9,629,664 | B2 | 4/2017 | Altarac et al. | |
| 9,814,495 | B2 | 11/2017 | Robie | |
| 9,844,402 | B2 | 12/2017 | Mayer et al. | |
| 10,912,591 | B2 | 2/2021 | Altarac et al. | |
| 2009/0287257 | A1* | 11/2009 | Hagen | A61B 17/7059 606/280 |
| 2012/0065690 | A1* | 3/2012 | Perrow | A61B 17/7059 606/294 |
| 2018/0103989 | A1* | 4/2018 | Altarac | A61B 17/7059 |
| 2019/0008995 | A1 | 1/2019 | Roth | |
| 2019/0357946 | A1* | 11/2019 | Sluder | A61B 17/8061 |
| 2021/0236176 | A1* | 8/2021 | Lewis | A61B 17/7059 |

* cited by examiner

*Primary Examiner* — Si Ming Ku

(74) *Attorney, Agent, or Firm* — UB Greensfelder LLP; Brian E. Turung

(57) ABSTRACT

A bone plate for use as a orthopedic implant.

32 Claims, 7 Drawing Sheets

20

20

20

20

20

20

20

20

20

CERVICAL PLATE

The present disclosure is a continuation in part of U.S. Design patent application Ser. No. 29/823,883 filed Jan. 20, 2022, which is fully incorporated herein by reference.

The present disclosure also claims priority on U.S. Provisional Application Ser. No. 63/303,126 filed Jan. 26, 2022, which is fully incorporated herein by reference.

The present disclosure also claims priority on U.S. Provisional Application Ser. No. 63/359,335 filed Jul. 8, 2022, which is fully incorporated herein by reference.

The present disclosure also claims priority on U.S. Provisional Application Ser. No. 63/410,015 filed Sep. 26, 2022, which is fully incorporated herein by reference.

The disclosure relates generally to medical devices and medical device applications, more particularly to orthopedic devices, and still more particularly to cervical plates and methods for using the cervical plate.

BACKGROUND

A cervical plate is a medically designed implant used during spinal instrumentation and fusion procedures to provide neck stability. Cervical plates can be used to enhance the rate of fusion and, in some cases, may reduce the need for external bracing following surgery.

Depending on the procedure and the number of spinal levels involved, one or more cervical plates can be implanted in the spine. The cervical plate is typically held in place by a plurality of screws that are set into adjacent vertebrae.

Cervical plates are commonly formed of titanium and cobalt chromium alloys because of the metal's high resistance to corrosion and fatigue, and such metal is MRI compatible. An example of a standard cobalt-chromium alloy used in cervical plates is MP35N (e.g., MP35N: 19-21 wt. % chromium, 34-36 wt. % nickel, 9-11 wt. % molybdenum, 1 wt. % max iron, 1 wt. % max titanium, 0.15 wt. % max manganese, 0.15 wt. % max silver, 0.025 wt. % max carbon, balance cobalt). Other types of standard cobalt-chromium alloys that can be used in cervical plates are Phynox and Elgiloy® alloy (38-42 wt. % cobalt, 18-22 wt. % chromium, 14-18 wt. % iron, 13-17 wt. % nickel, 6-8 wt. % molybdenum), and L605 alloy (18-22 wt. % chromium, 14-16 wt. % W, 9-11 wt. % nickel, balance cobalt). An example of a standard titanium alloy used in cervical plates is a standard TiAlV alloy (e.g., Ti-6Al-4V; 5.5-6.5 wt. % aluminum, 3.5-4.5 wt. % vanadium and balance titanium; 3.5-4.5 wt. % vanadium, 5.5-6.75 wt. % aluminum, 0.3 wt. % max iron, 0.2 wt. % max oxygen, 0.08 wt. % max carbon, 0.05 wt. % max nitrogen, 0.015 wt. % max hydrogen, 0.05 wt. % max yttrium, balance titanium). An example of a standard stainless steel used in many types of medical devices is 316L (17-19 wt. % chromium, 13-15 wt. % nickel, 2-4 wt. % molybdenum, 2 wt. % max manganese, 0.75 wt. % max silicon, 0.03 wt. % max carbon, balance iron).

Cervical plates are used in cervical fusion procedures that are commonly used to relieve pressure on nerves, nerve roots, or the spinal cord. During a cervical fusion procedure, an intervertebral disc is commonly removed, the empty space that was once occupied by the intervertebral disc is filled with bone graft, and a cervical plate is securely fit to cover the bone graft. The cervical plate keeps the bone graft in place and provides stability between the vertebrae above and below the graft site. This stability facilitates in fusion of the bone graft with the adjacent vertebrae.

Various prior art cervical plates are illustrated in U.S. Pat. Nos. 10,912,591; 9,844,402; 9,629,664; 9,149,311; 8,961,517; 8,778,001; 8,328,854; 7,815,666; 7,318,825; and 7,306,605, which are all incorporated herein by reference.

In view of the current state of the art, it would be desirable to provide a thinner cervical plate without sacrificing the strength of typical thicker cervical plates formed of titanium, stainless steel or cobalt-chromium alloys.

SUMMARY OF THE DISCLOSURE

The present disclosure is direct to a medical device in the form of an orthopedic fixation device to orthopedic devices, and still more particularly to cervical plates and methods for using the cervical plate.

In one non-limiting aspect of the present disclosure, there is provided a medical device in the form of a spinal cervical plate. The cervical plate can optionally be configured and dimensioned for attachment on the anterior portion of the cervical spine.

In another non-limiting aspect of the present disclosure, the cervical plate optionally includes one or more openings and/or one or more end indents that can be used by a physician to orient the cervical plate in position. In one non-limiting embodiment, the tool hole is a circular or generally circular opening and has a maximum diameter of 1-4 mm (and all values and ranges therebetween. Generally, the cross-sectional area of the tool opening is less than the openings in the cam recesses and/or the screw openings. Generally, the tool opening is spaced from the outer perimeter of the cervical plate and also spaced from the screw openings and the cam recesses.

In another non-limiting aspect of the present disclosure, the cervical plate optionally includes one or more cam recesses that are configured to receive a cam (not shown) that can be releasably connected to the top surface of the cervical plate. The number of cam recesses on the cervical plate and the shape, size, and/or configuration of the cam recess on the cervical plate are non-limiting. In one non-limiting size of the cam opening, the cam opening can be 2-6 mm (and all values and ranges therebetween). The cam openings in the cam recesses are generally spaced from the screw openings and the outer perimeter of the cervical plate.

In another non-limiting aspect of the present disclosure, the cervical plate screw openings optionally have a generally circular cross-sectional shape. In one non-limiting embodiment, the diameter of the one or more screw openings is 3-6 mm (and all values and ranges therebetween). The spacing of two or more adjacently positioned screw openings is generally 1.5-4.5 mm (and all values and ranges therebetween).

In another non-limiting aspect of the present disclosure, the inner surface of the one or more screw openings optionally has one or more concavely indented surfaces. One non-limiting purpose of the concavely indented surfaces is to orient the longitudinal axis of the screw at a particular angle relative to the body of the cervical plate when securing the cervical plate to the spine.

In another non-limiting aspect of the present disclosure, the cervical plate can include one or more pairs of screw openings, with each screw opening of the pair of screw openings residing on either side of the longitudinal central axis of the cervical plate. Each screw opening in the pair of openings may be spaced apart from its mate such that the screw opening of each pair reside equidistantly on each side of the central longitudinal axis of the cervical plate; however, this is not required.

In another non-limiting aspect of the present disclosure, the fastener that is used with the cervical plate can be oriented in the screw opening at various angles to the longitudinal axis of the screw opening. For example, the longitudinal axis of one or more of the fasteners can be ±0-8° (and all values and ranges therebetween) relative to the longitudinal axis of the screw opening along the transverse axis of the cervical plate. In another example, the longitudinal axis of the fasteners can be ±0-25° (and all values and ranges therebetween) relative to the longitudinal axis of the screw opening relative in the longitudinal axis of the cervical plate. As such, the screw openings can optionally have dual angulation.

In another non-limiting aspect of the present disclosure, the sides of the cervical plate can optionally have multiple arcuate regions that create generally wavy side edges of the cervical plate; however, it can be appreciated that such arcuate regions are not required. The radius of curvature is optionally 5-10 mm (and all values and ranges therebetween). Due to these optional arcuate regions, the width of the cervical plate varies along the longitudinal length of the cervical plate. When the cervical plate varies in width, the location of the screw openings can optionally be located at the regions having the larger width of the cervical plate. In another one non-limiting configuration, the thickness of the cervical plate at the location of the screw openings can optionally be thicker than at the regions that are absent the screw openings.

In another non-limiting aspect of the present disclosure, the cross-sectional area and/or width of the cervical plate may be different along the longitudinal length of the cervical plate. For example, the cross-sectional area in the region of the cervical plate that is widest (e.g., mid-longitudinal point of the cervical plate) can optionally have a greater cross-sectional area in the region of the cervical plate than compared to the narrower width regions of the cervical plate. In one non-limiting embodiment, the cross-sectional area in the region of the cervical plate that is widest is 10-40% (and all values and ranges therebetween) greater than the cross-sectional area in the region of the cervical plate that is narrowest. In one specific configuration, the cross-sectional area of the cervical plate along the longitudinal length of the cervical plate is 8-16 $mm^2$ (and all values and ranges therebetween). In another non-limiting configuration, the cross-sectional area of the cervical plate optionally varies along the longitudinal length of the cervical plate. In another non-limiting configuration, the maximum thickness of the cervical plate is 1-3 mm (and all values and ranges therebetween). In another non-limiting configuration, the thickness of the cervical plate varies along the longitudinal length and/or latitudinal length of the cervical plate. In another non-limiting configuration, the width of the cervical plate is 5-18 mm (and all values and ranges therebetween). In another non-limiting configuration, the width of the cervical plate varies along the longitudinal length of the cervical plate. In another non-limiting configuration, the cross-sectional area of the cervical plate along the longitudinal length of the cervical plate is 8.5-14 $mm^2$. In another non-limiting configuration, the cross-sectional area of the cervical plate optionally varies along the longitudinal length of the cervical plate.

In another non-limiting aspect of the present disclosure, when the screws are inserted into the screw openings, the screw opening can optionally be shaped to cause the longitudinal axis of the screw to be at some non-tangential angle relative to top surface of the cervical plate. In one non-limiting configuration, the screw openings located nearest to the end of the cervical plate are configured such that the longitudinal axis of the screw (when fully placed into the screw opening) is oriented ±2-15° (and all values and ranges therebetween) from a right angle to the top surface of the cervical plate (e.g., 75-88° relative to the top surface of the cervical plate). In another non-limiting configuration, the screw openings located in the mid-region of the cervical plate are configured such that the longitudinal axis of the screw (when fully placed into the screw opening) is oriented ±0-8° (and all values and ranges therebetween) from a right angle to the top surface of the cervical plate (e.g., 82-90° relative to the top surface of the cervical plate).

In another non-limiting aspect of the present disclosure, the cervical plate can optionally have dual angulation of the screw openings wherein two or more adjacently positioned screw openings along a longitudinal axis of the cervical plate have a central axis that is not parallel to one another, and two or more pairs of adjacently positioned screw openings along the transverse axis (e.g., axis that is perpendicular to the longitudinal axis) have a central axis that is not parallel to one another. Such an arrangement can be caused by the orientation of the screw openings in the cervical plate and/or by the curvature of the cervical plate along the longitudinal and/or transverse axis of the cervical plate.

In another and/or alternative non-limiting aspect of the disclosure, the cervical plate and/or the screw openings in the cervical plate can be configured to enable a fastener arrangement to be oriented a) along the central axis of the screw opening when fully inserted into the screw openings, or b) be oriented off-center from the central axis of the screw opening when fully inserted into the screw openings. The cervical plate having a plurality of screw openings with the same size and configuration can enable a) all of the fastener arrangement to be oriented in the same way relative to the central axis of the screw opening when fully inserted into the screw openings, or b) one or more of the fastener arrangements have a different orientation to other fastener arrangements when fully inserted into the screw openings. The cervical plate having a plurality of screw openings with the same size and configuration can also enable a) the central axis of all of the fastener arrangements to be parallel with one another when fully inserted into the screw openings, or b) the central axis of one or more of the fastener arrangements to be non-parallel (e.g., oriented inwardly toward one another, oriented outwardly from one another, etc.) with the central axis of one or more other fastener arrangements when fully inserted into the screw openings. The ability to enable the fastener arrangements to have the ability to be secured to the cervical plate in various orientations relative to the central axis of the bone while using the same screw opening configuration on the cervical plate is a significant advantage when attempting to secure the cervical plate to a bone since the desired location of insertion of the fastener arrangement to the bone when the cervical plate is positioned on the bone is not always along the central axis of the screw opening. The ability to custom orient the fastener arrangement relative to the central axis of one or more or all of the screw openings enables the proper insertion of the fastener arrangement in the bone once the cervical plate is properly positioned on the bone.

In another non-limiting aspect of the present disclosure, the screw openings and the top portion of the fasteners (e.g., screw, etc.) are optionally configured so at least a portion or all of the top of the fastener is flush or slightly recessed in the screw opening when the fastener is fully inserted into the screw opening.

In another non-limiting aspect of the present disclosure, one side of the cam recess optionally terminates at one or both screw openings located adjacent to the cam recess, and the cam recess includes a sloped surface located between such screw openings. When a sloped surface exists between the two screw openings, the slope surface is generally configured and oriented so that the slope surface does not engage the cam during rotation of the cam in the cam recess. A portion of one or more cam recesses can optionally include a cam opening that passes fully through the cervical plate. The diameter of the cam openings is optionally 2-5 mm (and all values and ranges therebetween). The cam recess can optionally be configured to include one or more cam stops to limit rotation of a cam in the cam recess. The cam recess is optionally located 1-3 mm from the outer peripheral edge of the cervical plate.

In another non-limiting aspect of the present disclosure, the outer peripheral edge of the cervical plate can include a plurality of undulations on each of the two longitudinal sides of the cervical plate. In one non-limiting arrangement, the angle of curvature of the undulation along the long axis is 6-15° (and all values and ranges therebetween), and the angle of curvature of the undulation along the short axis is 30-40° (and all values and ranges therebetween).

In another non-limiting aspect of the present disclosure, the cervical plate can be manufactured from any suitable biocompatible material, including metal, such as stainless steel, cobalt-chromium alloy, cobalt-chromium-molybdenum alloy, titanium-aluminum vanadium alloy, molybdenum-titanium alloy, molybdenum-rhenium alloy, molybdenum alloy, rhenium alloy, rhenium-chromium alloy, refractory metal alloy, rhenium-containing alloy, or other suitable metallic alloys. In accordance with one non-limiting embodiment, the cervical plate is formed of 50-100% (and all values and ranges therebetween) of the suitable biocompatible material.

In accordance with another and/or alternative non-limiting aspect of the present disclosure, there is provided a cervical plate partially or fully formed of a metal alloy that includes rhenium in a sufficient quantity as to create a "rhenium effect" in the metal alloy. As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. It has been found for many metal alloys (e.g., standard stainless steel, standard CoCr alloys, standard TiAlV alloys, standard aluminum alloys, standard nickel alloys, standard titanium alloys, standard tungsten alloys, standard molybdenum alloys, standard coper alloys, standard MP35N alloys, standard beryllium-copper alloys, etc.) results in improved ductility and/or tensile strength. It has been found that the addition of rhenium to a metal alloy can result in the formation of a twining alloy in the metal alloy that results in the overall ductility of the metal alloy to increase as the yield and tensile strength increases due to the reduction and/or work hardening of the metal alloy. The rhenium effect occurs when the atomic weight of rhenium in the metal alloy is at least 15% (e.g., 15 awt. % to 99 awt. % rhenium in the metal alloy and all values and ranges therebetween). For example, for standard stainless steel alloys, the rhenium effect can begin to be present when the stainless steel alloy is modified to include a rhenium amount of at least 5-10 wt. % (and all values and ranges therebetween) of the stainless steel alloy. For standard CoCr alloys, the rhenium effect can begin to be present when the CoCr alloy is modified to include a rhenium amount of at least 4.8-9.5 wt. % (and all values and ranges therebetween) of the CoCr alloy. For standard TiAlV alloys, the "rhenium effect" can begin to be present when the TiAlV alloy is modified to include a rhenium amount of at least 4.5-9 wt. % (and all values and ranges therebetween) of the TiAlV alloy. At can be appreciated, the rhenium content in the above examples can be greater than the minimum amount to create the "rhenium effect" in the metal alloy.

In accordance with another and/or alternative non-limiting aspect of the present disclosure, there is provided a cervical plate that is formed of 50-100% (and all values and ranges therebetween) of a metal alloy that includes rhenium in a sufficient amount to create a rhenium effect in the metal alloy. In one non-limiting embodiment, the metal alloy includes at least 15 awt % rhenium, and at least 0.1 wt. % (e.g., 0.1-96 wt. % and all values and ranges therebetween) of one or more of aluminum, bismuth, chromium, cobalt, copper, hafnium, iridium, iron, magnesium, manganese, molybdenum, nickel, niobium, osmium, rhodium, ruthenium, silicon, silver, tantalum, technetium, titanium, tungsten, vanadium, yttrium, and zirconium.

In accordance with another and/or alternative non-limiting aspect of the present disclosure, there is provided a cervical plate that is formed of 50-100% (and all values and ranges therebetween) of a refractory metal alloy. The refractory metal alloy may or may not include sufficient rhenium to create a rhenium effect in the refractory metal alloy. As defined herein, a refractory metal alloy is a metal alloy that includes at least 20 wt. % of one or more of molybdenum, rhenium, niobium, tantalum, or tungsten. Non-limiting metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc.

In accordance with another and/or alternative non-limiting aspect of the present disclosure, there is provided a cervical plate that is formed of 50-100% (and all values and ranges therebetween) of a metal alloy that includes rhenium in a sufficient amount to create a rhenium effect in the metal alloy, and the metal alloy is a standard stainless steel alloy that has been modified to include at least 15 awt. % rhenium.

In accordance with another and/or alternative non-limiting aspect of the present disclosure, there is provided a cervical plate that is formed of 50-100% (and all values and ranges therebetween) of a metal alloy that includes rhenium in a sufficient amount to create a rhenium effect in the metal alloy, and the metal alloy is a standard cobalt chromium alloy that has been modified to include at least 15 awt. % rhenium.

In accordance with another and/or alternative non-limiting aspect of the present disclosure, there is provided a cervical plate that is formed of 50-100% (and all values and ranges therebetween) of a metal alloy that includes rhenium in a sufficient amount to create a rhenium effect in the metal alloy, and the metal alloy is a standard TiAlV alloy that has been modified to include at least 15 awt. % rhenium.

Several non-limiting examples of metal alloys that can be used to partially or fully form the medical device are set forth below in weight percent:

| Component/ Wt. % | Ex. 1 | Ex. 2 | Ex. 3 | Ex. 4 |
|---|---|---|---|---|
| Ag | 0-40% | 0-40% | 0-40% | 0-40% |
| Al | 0-40% | 0-40% | 0-40% | 0-40% |
| Bi | 0-40% | 0-40% | 0-40% | 0-40% |
| Cr | 0-40% | 0-40% | 0-40% | 0-40% |
| Cu | 0-40% | 0-40% | 0-40% | 0-40% |
| Co | 0-60% | 0-60% | 0-60% | 0-60% |
| Fe | 0-80% | 0-80% | 0-80% | 0-80% |
| Hf | 0-40% | 0-40% | 0-40% | 0-40% |
| Ir | 0-40% | 0-40% | 0-40% | 0-40% |
| Mg | 0-40% | 0-40% | 0-40% | 0-40% |
| Mn | 0-40% | 0-40% | 0-40% | 0-40% |
| Mo | 10-98% | 20-95% | 30-95% | 40-95% |
| Nb | 0-80% | 0-80% | 0-80% | 0-80% |
| Ni | 0-60% | 0-60% | 0-60% | 0-60% |
| Os | 0-40% | 0-40% | 0-40% | 0-40% |
| Pt | 0-40% | 0-40% | 0-40% | 0-40% |
| Re | 5-98% | 10-90% | 20-80% | 30-70% |
| Rh | 0-40% | 0-40% | 0-40% | 0-40% |
| Si | 0-40% | 0-40% | 0-40% | 0-40% |
| Sn | 0-40% | 0-40% | 0-40% | 0-40% |
| Ta | 0-80% | 0-60% | 0-80% | 0-80% |
| Tc | 0-40% | 0-40% | 0-40% | 0-40% |
| Ti | 0-60% | 0-60% | 0-60% | 0-60% |
| V | 0-40% | 0-40% | 0-40% | 0-40% |
| W | 0-98% | 0-98% | 0-98% | 0-98% |
| Y | 0-40% | 0-40% | 0-40% | 0-40% |
| Zr | 0-40% | 0-40% | 0-40% | 0-40% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 5 | Ex. 6 | Ex. 7 | Ex. 8 |
|---|---|---|---|---|
| Ag | 0-20% | 0-20% | 0-20% | 0-20% |
| Al | 0-35% | 0-30% | 5-30% | 0-25% |
| Bi | 0-20% | 0-20% | 0-20% | 0-20% |
| Cr | 10-40% | 0-40% | 0-40% | 0-40% |
| Cu | 0-20% | 0-20% | 0-20% | 0-20% |
| Co | 10-60% | 0-60% | 0-60% | 0-60% |
| Fe | 0-80% | 30-80% | 0-80% | 0-70% |
| Hf | 0-20% | 0-20% | 0-20% | 0-20% |
| Ir | 0-20% | 0-20% | 0-20% | 0-20% |
| Mg | 0-20% | 0-20% | 0-20% | 0-20% |
| Mn | 0-20% | 0-40% | 0-20% | 0-20% |
| Mo | 0-60% | 0-60% | 0-80% | 0-70% |
| Nb | 0-60% | 0-60% | 0-65% | 20-60% |
| Ni | 0-60% | 5-55% | 0-52% | 0-50% |
| Os | 0-20% | 0-20% | 0-20% | 0-20% |
| Pt | 0-20% | 0-20% | 0-20% | 0-20% |
| Re | 4.5-98% | 4.5-90% | 4.5-80% | 4.5-70% |
| Rh | 0-20% | 0-20% | 0-20% | 0-20% |
| Si | 0-20% | 0-20% | 0-20% | 0-20% |
| Sn | 0-20% | 0-20% | 0-20% | 0-20% |
| Ta | 0-60% | 0-60% | 5-65% | 0-60% |
| Tc | 0-20% | 0-20% | 0-20% | 0-20% |
| Ti | 0-60% | 0-55% | 0-53% | 0-50% |
| V | 0-20% | 0-20% | 2-20% | 0-20% |
| W | 0-60% | 0-60% | 0-80% | 0-70% |
| Y | 0-20% | 0-20% | 0-20% | 0-20% |
| Zr | 0-20% | 0-20% | 0-20% | 5-20% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 9 | Ex. 10 | Ex. 11 | Ex. 12 |
|---|---|---|---|---|
| Ag | 0-5% | 0-5% | 0-5% | 0-5% |
| Al | 0-5% | 0-5% | 1-15% | 0-20% |

-continued

| | | | | |
|---|---|---|---|---|
| Bi | 0-5% | 0-5% | 0-5% | 0-5% |
| Cr | 1-28% | 1-30% | 0-5% | 0-30% |
| Cu | 0-20% | 0-5% | 0-5% | 0-25% |
| Co | 0-5% | 1-60% | 0-5% | 0-60% |
| Fe | 10-80% | 0-25% | 0-5% | 0-80% |
| Hf | 0-5% | 0-5% | 0-5% | 0-5% |
| Ir | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-8% | 0-25% | 0-5% | 0-98% |
| Nb | 0-5% | 0-5% | 0-5% | 0-95% |
| Ni | 1-20% | 1-45% | 0-5% | 0-50% |
| Os | 0-5% | 0-5% | 0-5% | 0-5% |
| Pt | 0-5% | 0-5% | 0-5% | 0-5% |
| Re | 5-20% | 4.8-20% | 4.5-20% | 4.5-20% |
| Rh | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-98% |
| Tc | 0-5% | 0-5% | 0-5% | 0-5% |
| Ti | 0-5% | 0-5% | 40-93% | 0-93% |
| V | 0-5% | 0-5% | 1-10% | 0-20% |
| W | 0-5% | 0-20% | 0-5% | 0-98% |
| Y | 0-5% | 0-5% | 0-5% | 0-5% |
| Zr | 0-5% | 0-5% | 0-5% | 0-5% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 13 | Ex. 14 | Ex. 15 | Ex. 16 |
|---|---|---|---|---|
| Mo | 40-80% | 40-80% | 40-80% | 40-80% |
| C | 0.01-0.3% | 0-0.3% | 0-0.3% | 0-0.3% |
| Co | ≤0.002% | ≤0.002% | ≤0.002% | ≤0.002% |
| $Cs_2O$ | 0-0.2% | 0-0.2% | 0.01-0.2% | 0-0.2% |
| Fe | ≤0.02% | ≤0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | ≤0.06% | ≤0.06% | ≤0.06% | ≤0.06% |
| Os | <1% | <1% | <1% | <1% |
| $La_2O_3$ | 0-32% | 0.1-2% | 0-2% | 0-2% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| Re | 7-49% | 7.5-49% | 7.5-49% | 7.5-49% |
| S | ≤0.008% | ≤0.008% | ≤0.008% | ≤0.008% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0-50% |
| $Y_2O_3$ | 0-1% | 0-1% | 0-1% | 0-1% |
| Zr | ≤1% | ≤1% | ≤1% | ≤1% |
| $ZrO_2$ | 0-3% | 0-3% | 0-3% | 0-3% |
| CNT | 0-10% | 0-10% | 0-10% | 0-10% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 17 | Ex. 18 | Ex. 19 |
|---|---|---|---|
| Mo | 40-80% | 40-80% | 40-80% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | ≤0.01% | ≤0.01% |

-continued

| | | | |
|---|---|---|---|
| Pt | ≤1% | ≤1% | ≤1% |
| Re | 7-49% | 7.5-49% | 7.5-49% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| CNT | 0-10% | 0-10% | 0-10% |
| C | <0.06 | <0.06 | <0.06 |
| N | <0.06 | <0.06 | <0.06 |
| O | <0.06 | <0.06 | <0.06 |

| Component/ Wt. % | Ex. 20 | Ex. 21 | Ex. 22 |
|---|---|---|---|
| Mo | 45-78% | 45-75% | 45-70% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 7-49% | 7.5-49% | 7.5-49% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| CNT | 0-10% | 0-10% | 0-10% |
| C | <0.06 | <0.06 | <0.06 |
| N | <0.06 | <0.06 | <0.06 |
| O | <0.06 | <0.06 | <0.06 |

| Component/ Wt. % | Ex. 23 | Ex. 24 | Ex. 25 | Ex. 26 |
|---|---|---|---|---|
| Mo | 35-80% | 35-80% | 35-70% | 35-65% |
| C | 0.05-0.15% | 0-0.15% | 0-0.15% | 0-0.15% |
| CsO | 0-0.2% | 0-0.2% | 0.04-0.1% | 0-0.2% |
| Hf | 0.8-1.4% | 0-2% | 0-2.5% | 0-2.5% |
| $La_2O_3$ | 0-2% | 0.3-0.7% | 0-2% | 0-2% |
| Re | 7-49% | 7-49% | 7.5-49% | 7.5-49% |
| Ta | 0-2% | 0-2% | 0-50% | 0-50% |
| W | 0-2% | 0-2% | 0-50% | 20-50% |
| $Y_2O_3$ | 0-1% | 0-1% | 0.3-0.5% | 0-1% |
| $ZrO_2$ | 0-3% | 0-3% | 0-3% | 0-3% |

| Component/ Wt. % | Ex. 27 | Ex. 28 | Ex. 29 |
|---|---|---|---|
| Mo | 40-60% | 35-60% | 30-60% |
| C | 0-0.15% | 0-0.15% | 0-0.15% |
| $Cs_2O$ | 0-0.2% | 0-0.2% | 0-0.2% |
| Hf | 0-2.5% | 0-2.5% | 0-2.5% |
| $La_2O_3$ | 0-2% | 0-2% | 0-2% |
| Re | 7-60% | 7.5-65% | 7.5-70% |
| Ta | 0-3% | 10-50% | 0-40% |
| W | 0-3% | 0-50% | 0-40% |
| $Y_2O_3$ | 0-1% | 0-1% | 0-1% |
| $ZrO_2$ | 1.2-1.8% | 0-3% | 0-3% |

| Component/ Wt. % | Ex. 30 | Ex. 31 | Ex. 32 |
|---|---|---|---|
| W | 20-80% | 60-80% | 20-78% |
| Re | 7.5-47.5% | 10-40% | 8-47.5% |

-continued

| | | | |
|---|---|---|---|
| Mo | 0-47.5% | <0.5% | 1-47.5% |
| Cu | <0.5% | <0.5% | <0.5% |
| C | ≤0.15% | ≤0.15% | ≤0.15% |
| Co | ≤0.002% | ≤0.002% | ≤0.002% |
| $Cs_2O$ | ≤0.2% | ≤0.2% | ≤0.2% |
| Fe | ≤0.02% | ≤0.02% | ≤0.02% |
| H | ≤0.002% | ≤0.002% | ≤0.002% |
| Hf | ≤0.5% | ≤0.5% | ≤0.5% |
| $La_2O_3$ | <0.5% | <0.5% | <0.5% |
| O | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | ≤0.01% | ≤0.01% |
| Pt | <0.5% | <0.5% | <0.5% |
| S | ≤0.008% | ≤0.008% | ≤0.008% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| $Y_2O_3$ | <0.5% | <0.5% | <0.5% |
| Zr | <0.5% | <0.5% | <0.5% |
| $ZrO_2$ | <0.5% | <0.5% | <0.5% |
| CNT | 0-10% | 0-10% | <0.5% |
| C | <0.06 | <0.06 | <0.06 |
| N | <0.06 | <0.06 | <0.06 |
| O | <0.06 | <0.06 | <0.06 |

| Component/ Wt. % | Ex. 33 | Ex. 34 | Ex. 35 |
|---|---|---|---|
| W | 20-80% | 60-80% | 20-75% |
| Re | 7.5-47.5% | 10-40% | 7.5-47.5% |
| Mo | 0-47.5% | <0.5% | 1-47.5% |

| Component/ Wt. % | Ex. 36 | Ex. 37 | Ex. 38 |
|---|---|---|---|
| W | 50.1-80% | 65-80% | 50.1-79% |
| Re | 10-40% | 10-35% | 10-40% |
| Mo | 0-40% | <0.5% | 1-30% |

| Component/ Wt. % | Ex. 39 | Ex. 40 | Ex. 41 |
|---|---|---|---|
| W | 20-49% | 20-49% | 20-49% |
| Re | 7.5-60% | 7.5-60% | 7.5-60% |
| Mo | 0-40% | 0-40% | 0-39% |

| Component/ Wt. % | Ex. 42 | Ex. 43 | Ex. 44 |
|---|---|---|---|
| Re | 5-98% | 60-95% | 80-90% |
| Mo | 0-80% | 0-40% | 0-20% |
| W | 0-80% | 0-40% | 0-20% |

| Component/ Wt. % | Ex. 45 | Ex. 46 | Ex. 47 |
|---|---|---|---|
| W | 20-49% | 20-49% | 20-49% |
| Re | 6-40% | 6-40% | 6-39% |
| Mo | 20-60% | 30-60% | 40-60% |

| Component/ Wt. % | Ex. 48 | Ex. 49 | Ex. 50 |
|---|---|---|---|
| W | 20-40% | 20-35% | 20-30% |
| Re | 6-40% | 6-40% | 6-40% |
| Mo | 0-40% | 10-40% | 31-40% |

| Component/ Wt. % | Ex. 51 | Ex. 52 | Ex. 53 | Ex. 54 |
|---|---|---|---|---|
| Re | 5-60% | 5-60% | 5-60% | 5-60% |
| Mo | 0-55% | 10-55% | 10-55% | 10-55% |
| Bi | 1-42 | 0-32 | 0-32 | 0-32 |
| Cr | 0-32 | 1-42 | 0-32 | 0-32 |
| Ir | 0-32 | 0-32 | 1-42 | 0-32 |
| Nb | 0-32 | 0-32 | 0-32 | 1-42 |

-continued

| | | | | |
|---|---|---|---|---|
| Ta | 0-32 | 0-32 | 0-32 | 0-32 |
| Ti | 0-32 | 0-32 | 0-32 | 0-32 |
| Y | 0-32 | 0-32 | 0-32 | 0-32 |
| Zr | 0-32 | 0-32 | 0-32 | 0-32 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 55 | Ex. 56 | Ex. 57 | Ex. 58 |
|---|---|---|---|---|
| Re | 5-60% | 5-60% | 5-60% | 5-60% |
| Mo | 15-55% | 15-55% | 15-55% | 15-55% |
| Bi | 0-32 | 0-32 | 0-32 | 0-32 |
| Cr | 0-32 | 0-32 | 0-32 | 0-32 |
| Ir | 0-32 | 0-32 | 0-32 | 0-32 |
| Nb | 0-32 | 0-32 | 0-32 | 0-32 |
| Ta | 1-42 | 0-32 | 0-32 | 0-32 |
| Ti | 0-32 | 1-42 | 0-32 | 0-32 |
| Y | 0-32 | 0-32 | 1-42 | 0-32 |
| Zr | 0-32 | 0-32 | 0-32 | 1-42 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 59 | Ex. 60 | Ex. 61 | Ex. 62 |
|---|---|---|---|---|
| Re | 41-59% | 41-59% | 41-59% | 41-59% |
| Mo | 18-45% | 18-45% | 18-45% | 18-45% |
| Bi | 1-42 | 0-32 | 0-32 | 0-32 |
| Cr | 0-32 | 1-42 | 0-32 | 0-32 |
| Ir | 0-32 | 0-32 | 1-42 | 0-32 |
| Nb | 0-32 | 0-32 | 0-32 | 1-42 |
| Ta | 0-32 | 0-32 | 0-32 | 0-32 |
| Ti | 0-32 | 0-32 | 0-32 | 0-32 |
| Y | 0-32 | 0-32 | 0-32 | 0-32 |
| Zr | 0-32 | 0-32 | 0-32 | 0-32 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 63 | Ex. 64 | Ex. 65 | Ex. 66 |
|---|---|---|---|---|
| Re | 41-59% | 41-59% | 41-59% | 41-59% |
| Mo | 18-45% | 18-45% | 18-45% | 18-45% |
| Bi | 0-32 | 0-32 | 0-32 | 0-32 |
| Cr | 0-32 | 0-32 | 0-32 | 0-32 |
| Ir | 0-32 | 0-32 | 0-32 | 0-32 |
| Nb | 0-32 | 0-32 | 0-32 | 0-32 |
| Ta | 1-42 | 0-32 | 0-32 | 0-32 |
| Ti | 0-32 | 1-42 | 0-32 | 0-32 |
| Y | 0-32 | 0-32 | 1-42 | 0-32 |
| Zr | 0-32 | 0-32 | 0-32 | 1-42 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 67 | Ex. 68 | Ex. 69 | Ex. 70 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 1-36 | 0-15 |
| Cr | 1-20 | 1-20 | 1-20 | 1-20 |
| Ir | 0-15 | 0-15 | 0-15 | 0-15 |
| Nb | 1-36 | 0-15 | 0-15 | 0-15 |
| Ta | 0-15 | 1-36 | 0-15 | 0-15 |
| Ti | 0-15 | 0-15 | 0-15 | 0-15 |
| Y | 0-15 | 0-15 | 0-15 | 0-15 |
| Zr | 0-15 | 0-15 | 0-15 | 1-36 |
| C | <0.06 | <0.06 | <0.06 | <0.06 |
| N | <0.06 | <0.06 | <0.06 | <0.06 |
| O | <0.06 | <0.06 | <0.06 | <0.06 |

-continued

| Component/ Wt. % | Ex. 71 | Ex. 72 | Ex. 73 | Ex. 74 |
|---|---|---|---|---|
| Re | 41-59% | 41-59% | 41-59% | 41-59% |
| Mo | 18-45% | 18-45% | 18-45% | 18-45% |
| Bi | 1-36 | 0-15 | 0-15 | 0-15 |
| Cr | 1-20 | 1-20 | 1-20 | 1-20 |
| Ir | 0-15 | 1-36 | 0-15 | 0-15 |
| Nb | 0-15 | 0-15 | 0-15 | 0-15 |
| Ta | 0-15 | 0-15 | 0-15 | 0-15 |
| Ti | 0-15 | 0-15 | 1-36 | 0-15 |
| Y | 0-15 | 0-15 | 0-15 | 1-36 |
| Zr | 0-15 | 0-15 | 0-15 | 0-15 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 75 | Ex. 76 | Ex. 77 | Ex. 78 |
|---|---|---|---|---|
| Re | 41-59% | 41-59% | 41-59% | 41-59% |
| Mo | 18-45% | 18-45% | 18-45% | 18-45% |
| Bi | 1-34 | 0-15 | 0-15 | 0-15 |
| Cr | 0-15 | 0-15 | 0-15 | 0-15 |
| Ir | 0-15 | 0-15 | 0-15 | 1-34 |
| Nb | 3-27 | 3-27 | 3-27 | 3-27 |
| Ta | 0-42 | 1-34 | 0-15 | 0-15 |
| Ti | 0-15 | 0-15 | 0-15 | 0-15 |
| Y | 0-15 | 0-15 | 0-15 | 0-15 |
| Zr | 0-15 | 0-15 | 3-27 | 0-15 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 79 | Ex. 80 | Ex. 81 | Ex. 82 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 0-15 | 0-15 |
| Cr | 0-15 | 0-15 | 0-15 | 0-15 |
| Ir | 0-15 | 1-34 | 0-15 | 0-15 |
| Nb | 0-15 | 0-15 | 0-15 | 0-15 |
| Ta | 1-34 | 0-15 | 3-27 | 0-15 |
| Ti | 0-15 | 0-15 | 0-15 | 0-15 |
| Y | 0-15 | 0-15 | 0-15 | 3-27 |
| Zr | 3-27 | 3-27 | 3-27 | 3-27 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 83 | Ex. 84 | Ex. 85 | Ex. 86 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 0-15 | 0-15 |
| Cr | 0-15 | 0-15 | 0-15 | 1-10 |
| Ir | 1-34 | 0-25 | 3-27 | 0-15 |
| Nb | 0-15 | 3-27 | 0-15 | 0-15 |
| Ta | 0-15 | 0-15 | 1-34 | 0-15 |
| Ti | 0-15 | 0-15 | 0-15 | 0-15 |
| Y | 3-27 | 3-27 | 0-15 | 0-15 |
| Zr | 0-15 | 0-15 | 3-27 | 1-12 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 87 | Ex. 88 | Ex. 89 | Ex. 90 |
|---|---|---|---|---|
| Re | 50-75% | 55-75% | 60-75% | 65-75% |
| Cr | 25-50% | 25-45% | 25-40% | 25-35% |
| Mo | 0-25% | 0-25% | 0-25% | 0-25% |
| Bi | 0-25% | 0-25% | 0-25% | 0-25% |
| Cr | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |

-continued

| | | | | |
|---|---|---|---|---|
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |
| Ag | 0-25% | 0-25% | 0-25% | 0-25% |
| Al | 0-25% | 0-25% | 0-25% | 0-22% |
| Co | 0-25% | 0-25% | 0-25% | 0-25% |
| Fe | 0-25% | 0-25% | 0-25% | 0-25% |
| Mg | 0-25% | 0-25% | 0-25% | 0-25% |
| Ni | 0-25% | 0-25% | 0-25% | 0-25% |
| Pt | 0-25% | 0-25% | 0-25% | 0-25% |
| Si | 0-25% | 0-25% | 0-25% | 0-25% |
| Sn | 0-25% | 0-25% | 0-25% | 0-25% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 91 | Ex. 92 | Ex. 93 | Ex. 94 |
|---|---|---|---|---|
| Re | 50-72% | 55-72% | 60-72% | 65-72% |
| Cr | 28-50% | 28-45% | 28-40% | 28-35% |
| Mo | 0-25% | 0-25% | 0-25% | 0-25% |
| Bi | 0-10% | 0-10% | 0-10% | 0-10% |
| Cr | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 95 | Ex. 96 | Ex. 97 | Ex. 98 |
|---|---|---|---|---|
| Re | 50-70% | 55-70% | 60-70% | 65-70% |
| Cr | 30-50% | 30-45% | 30-40% | 30-35% |
| Mo | 0-10% | 0-10% | 0-10% | 0-10% |
| Bi | 0-10% | 0-10% | 0-10% | 0-10% |
| Cr | 0-10% | 0-10% | 0-10% | 0-10% |

-continued

| | | | | |
|---|---|---|---|---|
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| $Cs_2O$ | 0-1% | 0-1% | 0-1% | 0-1% |
| $La_2O3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 99 | Ex. 100 | Ex. 101 | Ex. 102 |
|---|---|---|---|---|
| Re | 50-67.5% | 55-67.5% | 60-67.5% | 65-67.5% |
| Cr | 32.5-50% | 32.5-45% | 32.5-40% | 32.5-35% |
| Mo | 0-10% | 0-10% | 0-10% | 0-10% |
| Bi | 0-10% | 0-10% | 0-10% | 0-10% |
| Cr | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 103 | Ex. 104 | Ex. 105 | Ex. 106 |
|---|---|---|---|---|
| Re | 50-67.5% | 55-67.5% | 60-67.5% | 65-67.5% |
| Cr | 32.5-50% | 32.5-45% | 32.5-40% | 32.5-35% |

-continued

| | | | | |
|---|---|---|---|---|
| Mo | 0-5% | 0-5% | 0-5% | 0-5% |
| Bi | 0-5% | 0-5% | 0-5% | 0-5% |
| Cr | 0-5% | 0-5% | 0-5% | 0-5% |
| Ir | 0-5% | 0-5% | 0-5% | 0-5% |
| Nb | 0-5% | 0-5% | 0-5% | 0-5% |
| Ta | 0-5% | 0-5% | 0-5% | 0-5% |
| V | 0-5% | 0-5% | 0-5% | 0-5% |
| W | 0-5% | 0-5% | 0-5% | 0-5% |
| Mn | 0-5% | 0-5% | 0-5% | 0-5% |
| Tc | 0-5% | 0-5% | 0-5% | 0-5% |
| Ru | 0-5% | 0-5% | 0-5% | 0-5% |
| Rh | 0-5% | 0-5% | 0-5% | 0-5% |
| Hf | 0-5% | 0-5% | 0-5% | 0-5% |
| Os | 0-5% | 0-5% | 0-5% | 0-5% |
| Cu | 0-5% | 0-5% | 0-5% | 0-5% |
| Ir | 0-5% | 0-5% | 0-5% | 0-5% |
| Ti | 0-5% | 0-5% | 0-5% | 0-5% |
| Y | 0-5% | 0-5% | 0-5% | 0-5% |
| Zr | 0-5% | 0-5% | 0-5% | 0-5% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |
| Pt | 0-5% | 0-5% | 0-5% | 0-5% |
| Si | 0-5% | 0-5% | 0-5% | 0-5% |
| Sn | 0-5% | 0-5% | 0-5% | 0-5% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 107 | Ex. 108 | Ex. 109 | Ex. 110 |
|---|---|---|---|---|
| Mo | 40-95% | 40-95% | 40-95% | 40-95% |
| C | 0.01-0.3% | 0-0.3% | 0-0.3% | 0-0.3% |
| Co | ≤0.002% | ≤0.002% | ≤0.002% | ≤0.002% |
| $Cs_2O$ | 0-0.2% | 0-0.2% | 0.01-0.2% | 0-0.2% |
| Fe | ≤0.02% | ≤0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | ≤0.06% | ≤0.06% | ≤0.06% | ≤0.06% |
| Os | ≤1% | ≤1% | ≤1% | ≤1% |
| $La_2O_3$ | 0-2% | 0.1-2% | 0-2% | 0-2% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| Re | 5-40% | 5-40% | 5-40% | 5-40% |
| S | ≤0.008% | ≤0.008% | ≤0.008% | ≤0.008% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0-50% |
| $Y_2O_3$ | 0-1% | 0-1% | 0-1% | 0-1% |
| Zr | ≤1% | ≤1% | ≤1% | ≤1% |
| $ZrO_2$ | 0-3% | 0-3% | 0-3% | 0-3% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |
| Sn | 0-5% | 0-5% | 0-5% | 0-5% |
| CNT | 0-10% | 0-10% | 0-10% | 0-10% |

| Component/ Wt. % | Ex. 111 | Ex. 112 | Ex. 113 |
|---|---|---|---|
| Mo | 40-95% | 40-95% | 40-95% |
| C | 0-0.3% | 0-0.3% | 0-0.3% |
| Co | ≤0.002% | ≤0.002% | ≤0.002% |
| $Cs_2O$ | 0-0.2% | 0.01-0.2% | 0-0.2% |

-continued

| | | | |
|---|---|---|---|
| H | ≤0.02% | ≤0.02% | ≤0.02% |
| Hf | 0-2.5% | 0-2.5% | 0-2.5% |
| O | ≤0.06% | ≤0.06% | ≤0.06% |
| Os | ≤1% | ≤1% | ≤1% |
| La2O3 | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 5-40% | 5-40% | 5-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | 0-10% |

| Component/ Wt. % | Ex. 114 | Ex. 115 | Ex. 116 |
|---|---|---|---|
| Mo | 60-95% | 60-95% | 60-90% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 5-40% | 5-40% | 10-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | 0-10% |

| Component/ Wt. % | Ex. 117 | Ex. 118 | Ex. 119 | Ex. 120 |
|---|---|---|---|---|
| Mo | 60-95% | 60-95% | 50-95% | 40-80% |
| C | 0.05-0.15% | 0-0.15% | 0-0.15% | 0-0.15% |
| $Cs_2O$ | 0-0.2% | 0-0.2% | 0.04-0.1% | 0-0.2% |
| Hf | 0.8-1.4% | 0-2% | 0-2.5% | 0-2.5% |
| $La_2O_3$ | 0-2% | 0.3-0.7% | 0-2% | 0-2% |
| Re | 5-40% | 5-40% | 5-40% | 5-40% |
| Ta | 0-2% | 0-2% | 0-50% | 0-50% |
| w | 0-2% | 0-2% | 0-50% | 20-50% |
| $Y_2O_3$ | 0-1% | 0-1% | 0.3-0.5% | 0-1% |
| $ZrO_2$ | 0-3% | 0-3% | 0-3% | 0-3% |

| Component/ Wt. % | Ex. 121 | Ex. 122 | Ex. 123 |
|---|---|---|---|
| Mo | 97-95% | 50-90% | 60-95% |
| C | 0-0.15% | 0-0.15% | 0-0.15% |
| $Cs_2O$ | 0-0.2% | 0-0.2% | 0-0.2% |

-continued

| | | | |
|---|---|---|---|
| Hf | 0-2.5% | 0-2.5% | 0-2.5% |
| $La_2O_3$ | 0-2% | 0-2% | 0-2% |
| Re | 5-30 | 5-40% | 5-40% |
| Ta | 0-3% | 10-50% | 0-40% |
| W | 0-3% | 0-50% | 0-40% |
| $Y_2O_3$ | 0-1% | 0-1% | 0-1% |
| $ZrO_2$ | 1.2-1.8% | 0-3% | 0-3% |

| Component/ Wt. % | Ex. 124 | Ex. 125 | Ex. 126 |
|---|---|---|---|
| W | 20-95% | 60-95% | 20-80% |
| Re | 5-47.5% | 5-40% | 5-47.5% |
| Mo | 0-47.5% | <0.5% | 1-47.5% |
| Cu | <0.5% | <0.5% | <0.5% |
| C | ≤0.15% | ≤0.15% | ≤0.15% |
| Co | ≤0.002% | ≤0.002% | ≤0.002% |
| $Cs_2O$ | ≤0.2% | ≤0.2% | ≤0.2% |
| Fe | ≤0.02% | ≤0.02% | ≤0.02% |
| H | ≤0.002% | ≤0.002% | ≤0.002% |
| Hf | <0.5% | <0.5% | <0.5% |
| $La_2O_3$ | <0.5% | <0.5% | <0.5% |
| O | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | ≤0.01% | ≤0.01% |
| Pt | <0.5% | <0.5% | <0.5% |
| S | ≤0.008% | ≤0.008% | ≤0.008% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| $Y_2O_3$ | <0.5% | <0.5% | <0.5% |
| Zr | <0.5% | <0.5% | <0.5% |
| $ZrO_2$ | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | <0.5%. |

| Component/ Wt. % | Ex. 127 | Ex. 128 | Ex. 129 | Ex. 130 |
|---|---|---|---|---|
| W | 1-94.9% | 1-94.9% | 1-94.9% | 10-95% |
| Cu | 0.1-94% | 0.1-94% | 0.1-94% | 1-84% |
| C | 0.01-0.3% | 0-0.3% | 0-0.3% | 0-0.3% |
| Co | ≤0.002% | ≤0.002% | ≤0.002% | ≤0.002% |
| $Cs_2O$ | 0-0.2% | 0-0.2% | 0.01-0.2% | 0-0.2% |
| Fe | ≤0.02% | ≤0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | ≤0.06% | ≤0.06% | ≤0.06% | ≤0.06% |
| Os | ≤1% | ≤1% | ≤1% | ≤1% |
| $La_2O_3$ | 0-2% | 0.1-2% | 0-2% | 0-2% |
| Mo | 0-5% | 0.1-3% | 0-2% | 0-3% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| Re | 5-40% | 5-40% | 5-40% | 6-40% |
| S | ≤0.008% | ≤0.008% | ≤0.008% | ≤0.008% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| $Y_2O_3$ | 0-1% | 0-1% | 0.1-1% | 0-1% |
| Zr | ≤1% | ≤1% | ≤1% | ≤1% |
| $ZrO_2$ | 0-3% | 0-3% | 0-3% | 0-3% |
| Ag | 0-5% | 0-5% | 0-5% | 0-5% |
| Al | 0-5% | 0-5% | 0-5% | 0-5% |
| Fe | 0-5% | 0-5% | 0-5% | 0-5% |
| Mg | 0-5% | 0-5% | 0-5% | 0-5% |

-continued

| | | | | |
|---|---|---|---|---|
| Ni | 0-5% | 0-5% | 0-5% | 0-5% |
| Si | 0-5% | 0-5% | 0-5% | 0-5% |
| CNT | 0-10% | 0-10% | 0-10% | 0-10% |

| Component/ Wt. % | Ex. 131 | Ex. 132 | Ex. 133 |
|---|---|---|---|
| W | 20-96% | 25-92% | 30-88% |
| Cu | 2-74% | 2-68% | 5-62% |
| C | 0-0.3% | 0-0.3% | 0-0.3% |
| Co | ≤0.002% | ≤0.002% | ≤0.002% |
| $Cs_2O$ | ≤0.02% | ≤0.02% | ≤0.02% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| Mo | 0-3% | 0-2% | 0-1% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 6-40% | 7-40% | 8-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | 0-10% |

| Component/ Wt. % | Ex. 134 | Ex. 135 | Ex. 136 | Ex. 137 |
|---|---|---|---|---|
| W | 25-88% | 35-87% | 40-86% | 50-85% |
| Cu | 5-68% | 5-57% | 5-51% | 5-40% |
| C | 0.05-0.15% | 0-0.15% | 0-0.15% | 0-0.15% |
| $Cs_2O$ | 0-0.2% | 0-0.2% | 0.04-0.1% | 0-0.2% |
| Hf | 0.8-1.4% | 0-2.5% | 0-2.5% | 0-2.5% |
| $La_2O_3$ | 7-20% | 8-20% | 9-20% | 10-20% |
| Re | 0-40% | 0-40% | 0-40% | 0-40% |
| Ta | 0-50% | 0-50% | 0-50% | 0-50% |
| $Y_2O_3$ | 0-1% | 0-1% | 0.3-0.5% | 0-1% |
| $ZrO_2$ | 0-3% | 0-3% | 0-3% | 0-3% |

| Component/ Wt. % | Ex. 138 | Ex. 139 | Ex. 140 |
|---|---|---|---|
| W | 55-88% | 60-87% | 70-86% |
| Cu | 1-34% | 1-28% | 1-17% |
| C | 0-0.15% | 0-0.15% | 0-0.15% |
| $Cs_2O$ | 0-0.2% | 0-0.2% | 0-0.2% |
| Hf | 0-2.5% | 0-2.5% | 0-2.5% |
| $La_2O_3$ | 0-2% | 0-2% | 0-2% |
| Re | 11-40% | 12-40% | 13-40% |
| Ta | 0-50% | 10-50% | 0-50% |
| W | 0-50% | 0-50% | 0-50% |
| $Y_2O_3$ | 0-1% | 0-1% | 0-1% |
| $ZrO_2$ | 1.2-1.8% | 0-3% | 0-3% |

| Component/ Wt. % | Ex. 141 | Ex. 142 | Ex. 143 |
|---|---|---|---|
| Ti | 55-66% | 65-76% | 70-76% |
| Mo | 20-41% | 20-31% | 20-26% |
| Re | 4-20% | 4-20% | 4-20% |
| Yt | <0.5% | <0.5% | <0.5% |
| Nb | <0.5% | <0.5% | <0.5% |
| Co | <0.5% | <0.5% | <0.5% |
| Cr | <0.5% | <0.5% | <0.5% |
| Zr | <0.5% | <0.5% | <0.5% |

-continued

| | | | |
|---|---|---|---|
| C | ≤0.15% | ≤0.15% | ≤0.15% |
| O | ≤0.06% | ≤0.06% | ≤0.06% |
| N | ≤20 ppm | ≤20 ppm | ≤20 ppm |

| Component/ Wt. % | Ex. 144 | Ex. 145 | Ex. 146 |
|---|---|---|---|
| W | 20-95% | 60-85% | 20-84% |
| Re | 5-47.5% | 15-40% | 5-47.5% |
| Mo | 0-47.5% | <0.5% | 1-47.5% |

| Component/ Wt. % | Ex. 147 | Ex. 148 | Ex. 149 |
|---|---|---|---|
| W | 50.1-93% | 65-92% | 70-90% |
| Re | 7-40% | 8-35% | 9-30% |
| Mo | 0-40% | <0.5% | 1-30% |

| Component/ Wt. % | Ex. 150 | Ex. 151 | Ex. 152 |
|---|---|---|---|
| W | 20-49% | 20-49% | 20-49% |
| Re | 5-40% | 5-40% | 5-39% |
| Mo | 20-60% | 30-60% | 40-60% |

| Component/ Wt. % | Ex. 153 | Ex. 154 | Ex. 155 |
|---|---|---|---|
| W | 20-40% | 20-35% | 20-30% |
| Re | 7-40% | 10-40% | 25-40% |
| Mo | 0-40% | 10-40% | 25-40% |

| Component/ Wt. % | Ex. 156 | Ex. 157 | Ex. 158 |
|---|---|---|---|
| W | 20-95% | 60-93% | 20-80% |
| Re | 5-47.5% | 7-40% | 5-47.5% |
| Mo | 0-47.5% | <0.5% | 1-47.5% |
| Cu | <0.5% | <0.5% | <0.5% |
| C | ≤0.15% | ≤0.15% | ≤0.15% |
| Co | ≤0.002% | ≤0.002% | ≤0.002% |
| $Cs_2O$ | ≤0.2% | ≤0.2% | ≤0.2% |
| Fe | ≤0.02% | ≤0.02% | ≤0.02% |
| H | ≤0.002% | ≤0.002% | ≤0.002% |
| Hf | <0.5% | <0.5% | <0.5% |
| $La_2O_3$ | <0.5% | <0.5% | <0.5% |
| O | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | ≤0.01% | ≤0.01% |
| Pt | <0.5% | <0.5% | <0.5% |
| S | ≤0.008% | ≤0.008% | ≤0.008% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| $Y_2O_3$ | <0.5% | <0.5% | <0.5% |
| Zr | <0.5% | <0.5% | <0.5% |
| $ZrO_2$ | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | <0.5% |

| Component/ Wt. % | Ex. 159 | Ex. 160 | Ex. 161 | Ex. 162 |
|---|---|---|---|---|
| Ag | 0-10% | 0-10% | 0-10% | 0-10% |
| Al | 0-10% | 0-10% | 0-10% | 2-10% |
| B | 0-10% | 0-10% | 0-10% | 0-10% |
| Bi | 0-10% | 0-10% | 0-10% | 0-10% |
| Cr | 2-30% | 10-30% | 0-20% | 0-20% |
| Cu | 0-10% | 0-10% | 0-10% | 0-10% |
| Co | 0-10% | 32-70% | 0-10% | 0-10% |
| Fe | 50-80% | 0-20% | 0-10% | 0-10% |

-continued

| | | | | |
|---|---|---|---|---|
| Hf | 0-10% | 0-10% | 0-10% | 0-10% |
| Ir | 0-10% | 0-10% | 0-10% | 0-10% |
| La | 0-10% | 0-10% | 0-10% | 0-10% |
| Mg | 0-10% | 0-10% | 0-10% | 0-10% |
| Mn | 0-20% | 0-10% | 0-10% | 0-10% |
| Mo | 0-10% | 0-30% | 0-16% | 0-16% |
| Nb | 0-10% | 0-10% | 0-10% | 0-10% |
| Ni | 0.1-30% | 0.1-40% | 0-10% | 0-10% |
| Os | 0-10% | 0-10% | 0-10% | 0-10% |
| Pt | 0-10% | 0-10% | 0-10% | 0-10% |
| Re | 5-40% | 4.8-40% | 4.5-80% | 4.5-80% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-12% | 0-12% |
| Ta | 0-10% | 0-10% | 0-10% | 0-10% |
| Tc | 0-10% | 0-10% | 0-10% | 0-10% |
| Ti | 0-10% | 0-10% | 70-91.5% | 70-91.5% |
| V | 0-10% | 0-10% | 0-10% | 0.01-10% |
| W | 0-10% | 0-20% | 0-10% | 0-10% |
| Y | 0-10% | 0-10% | 0-10% | 0-10% |
| Zr | 0-10% | 0-10% | 0-10% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 163 | Ex. 164 | Ex. 165 | Ex. 166 |
|---|---|---|---|---|
| Ag | 0-10% | 0-10% | 0-10% | 0-10% |
| Al | 0-10% | 0-10% | 0-10% | 0-10% |
| B | 0-10% | 0-10% | 0-10% | 0-10% |
| Bi | 0-10% | 0-10% | 0-10% | 0-10% |
| Cr | 0-10% | 0-20% | 0-20% | 0-10% |
| Cu | 0-10% | 0-10% | 0-50% | 0-10% |
| Co | 0-10% | 0-10% | 0-10% | 0-10% |
| Fe | 0-10% | 0-10% | 0-10% | 0-10% |
| Hf | 0-10% | 0-10% | 0-10% | 0-10% |
| Ir | 0-10% | 0-10% | 0-10% | 0-12% |
| La | 0-10% | 0-10% | 0-10% | 0-10% |
| Mg | 0-10% | 0-10% | 0-10% | 0-10% |
| Mn | 0-10% | 0-10% | 0-10% | 0-10% |
| Mo | 0-55% | 40-93% | 0-50% | 0-20% |
| Nb | 0-10% | 0-10% | 0-10% | 40-85% |
| Ni | 0-45% | 0-10% | 0-10% | 0-10% |
| Os | 0-10% | 0-10% | 0-10% | 0-10% |
| Pt | 0-10% | 0-10% | 0-10% | 0-10% |
| Re | 14-40% | 7-40% | 7-40% | 7-40% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-10% | 0-10% |
| Ta | 35-84% | 0-50% | 0-50% | 0-35% |
| Tc | 0-10% | 0-10% | 0-10% | 0-10% |
| Ti | 0-10% | 0-10% | 0-10% | 0-10% |
| V | 0-10% | 0-10% | 0-10% | 0-10% |
| W | 0.1-25% | 0-50% | 14-10% | 0-15% |
| Y | 0-10% | 0-10% | 0-10% | 0-10% |
| Zr | 0-10% | 0-10% | 0-50% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 167 | Ex. 168 | Ex. 169 | Ex. 170 |
|---|---|---|---|---|
| Ag | 0-10% | 0-10% | 0-5% | 0-5% |
| Al | 0-10% | 0-10% | 0-5% | 5-7% |
| B | 0-10% | 0-10% | 0-5% | 0-5% |
| Bi | 0-10% | 0-10% | 0-5% | 0-5% |
| Cr | 0-10% | 1-95% | 12-28% | 0-5% |

-continued

| | | | | |
|---|---|---|---|---|
| Cu | 0-10% | 0-10% | 0-5% | 0-5% |
| Co | 0-10% | 0-10% | 36-68% | 0-5% |
| Fe | 0-10% | 0-10% | 0-18% | 0-5% |
| Hf | 0-10% | 0-10% | 0-5% | 0-5% |
| Ir | 0-10% | 0-10% | 0-5% | 0-5% |
| La | 0-10% | 0-10% | 0-5% | 0-5% |
| Mg | 0-10% | 0-10% | 0-5% | 0-5% |
| Mn | 0-10% | 0-10% | 0-5% | 0-5% |
| Mo | 0-10% | 0-20% | 0-12% | 0-5% |
| Nb | 0-10% | 0-10% | 0-5% | 0-5% |
| Ni | 30-58% | 0-10% | 9-36% | 0-5% |
| Os | 0-10% | 0-10% | 0-5% | 0-5% |
| Pt | 0-10% | 0-10% | 0-5% | 0-5% |
| Re | 5-40% | 5-40% | 4.8-40% | 4.5-40% |
| Rh | 0-10% | 0-10% | 0-5% | 0-5% |
| Se | 0-10% | 0-10% | 0-5% | 0-5% |
| Si | 0-10% | 0-10% | 0-5% | 0-5% |
| Sn | 0-10% | 0-10% | 0-5% | 0-5% |
| Ta | 0-10% | 0-10% | 0-5% | 0-5% |
| Tc | 0-10% | 0-10% | 0-5% | 0-5% |
| Ti | 30-58% | 0-40% | 0-5% | 70-91.5% |
| V | 0-10% | 0-10% | 0-5% | 3-6% |
| W | 0-10% | 0-10% | 0-16% | 0-5% |
| Y | 0-10% | 0-10% | 0-5% | 0-5% |
| Zr | 0-10% | 0-20% | 0-5% | 0-5% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/ Wt. % | Ex. 171 | Ex. 172 | Ex. 173 | Ex. 174 |
|---|---|---|---|---|
| Ag | 0-8% | 0-8% | 0-8% | 0-8% |
| Al | 0-8% | 0-8% | 0-8% | 2-10% |
| B | 0-8% | 0-8% | 0-8% | 0-8% |
| Bi | 0-8% | 0-8% | 0-8% | 0-8% |
| Cr | 2-30% | 10-30% | 0-20% | 0-20% |
| Cu | 0-8% | 0-8% | 0-8% | 0-8% |
| Co | 0-8% | 32-70% | 0-8% | 0-8% |
| Fe | 50-80% | 0-20% | 0-8% | 0-8% |
| Hf | 0-8% | 0-8% | 0-8% | 0-8% |
| Ir | 0-8% | 0-8% | 0-8% | 0-8% |
| La | 0-8% | 0-8% | 0-8% | 0-8% |
| Mg | 0-8% | 0-8% | 0-8% | 0-8% |
| Mn | 0-20% | 0-8% | 0-8% | 0-8% |
| Mo | 0-8% | 0-30% | 0-16% | 0-16% |
| Nb | 0-8% | 0-8% | 0-8% | 0-8% |
| Ni | 0.1-30% | 0.1-40% | 0-8% | 0-8% |
| Os | 0-8% | 0-8% | 0-8% | 0-8% |
| Pt | 0-8% | 0-8% | 0-8% | 0-8% |
| Re | 5-40% | 4.8-40% | 4.5-80% | 4.5-80% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-12% | 0-12% |
| Ta | 0-8% | 0-8% | 0-8% | 0-8% |
| Tc | 0-8% | 0-8% | 0-8% | 0-8% |
| Ti | 0-8% | 0-8% | 70-91.5% | 70-91.5% |
| V | 0-8% | 0-8% | 0-8% | 0.01-10% |
| W | 0-8% | 0-20% | 0-8% | 0-8% |
| Y | 0-8% | 0-8% | 0-8% | 0-8% |
| Zr | 0-8% | 0-8% | 0-8% | 0-8% |

| Component/ Wt. % | Ex. 175 | Ex. 176 | Ex. 177 | Ex. 178 |
|---|---|---|---|---|
| Ag | 0-8% | 0-8% | 0-8% | 0-8% |
| Al | 0-8% | 0-8% | 0-8% | 0-8% |
| B | 0-8% | 0-8% | 0-8% | 0-8% |
| Bi | 0-8% | 0-8% | 0-8% | 0-8% |
| Cr | 0-8% | 0-20% | 0-20% | 0-8% |
| Cu | 0-8% | 0-8% | 0-50% | 0-8% |
| Co | 0-8% | 0-8% | 0-8% | 0-8% |
| Fe | 0-8% | 0-8% | 0-8% | 0-8% |
| Hf | 0-8% | 0-8% | 0-8% | 0-8% |

-continued

| | | | | |
|---|---|---|---|---|
| Ir | 0-8% | 0-8% | 0-8% | 0-12% |
| La | 0-8% | 0-8% | 0-8% | 0-8% |
| Mg | 0-8% | 0-8% | 0-8% | 0-8% |
| Mn | 0-8% | 0-8% | 0-8% | 0-8% |
| Mo | 0-55% | 40-93% | 0-50% | 0-20% |
| Nb | 0-8% | 0-8% | 0-8% | 40-85% |
| Ni | 0-45% | 0-8% | 0-8% | 0-8% |
| Os | 0-8% | 0-8% | 0-8% | 0-8% |
| Pt | 0-8% | 0-8% | 0-8% | 0-8% |
| Re | 14-40% | 7-40% | 7-40% | 7-40% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-8% | 0-8% |
| Ta | 35-84% | 0-50% | 0-50% | 0-35% |
| Tc | 0-8% | 0-8% | 0-8% | 0-8% |
| Ti | 0-8% | 0-8% | 0-8% | 0-8% |
| V | 0-8% | 0-8% | 0-8% | 0-8% |
| W | 0.1-25% | 0-50% | 14-10% | 0-15% |
| Y | 0-8% | 0-8% | 0-8% | 0-8% |
| Zr | 0-8% | 0-8% | 0-50% | 0-8% |

| Component/ Wt. % | Ex. 179 | Ex. 180 | Ex. 181 | Ex. 182 |
|---|---|---|---|---|
| Ag | 0-5% | 0-5% | 0-5% | 0-5% |
| Al | 0-5% | 0-5% | 0-5% | 5-7% |
| B | 0-5% | 0-5% | 0-5% | 0-5% |
| Bi | 0-5% | 0-5% | 0-5% | 0-5% |
| Cr | 0-5% | 1-95% | 12-28% | 0-5% |
| Cu | 0-5% | 0-5% | 0-5% | 0-5% |
| Co | 0-5% | 0-5% | 36-68% | 0-5% |
| Fe | 0-5% | 0-5% | 0-18% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-20% | 0-12% | 0-5% |
| Nb | 0-5% | 0-5% | 0-5% | 0-5% |
| Ni | 30-58% | 0-5% | 9-36% | 0-5% |
| Os | 0-5% | 0-5% | 0-5% | 0-5% |
| Pt | 0-5% | 0-5% | 0-5% | 0-5% |
| Re | 5-40% | 5-40% | 4.8-40% | 4.5-40% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 30-58% | 0-40% | 0-5% | 70-91.5% |
| V | 0-5% | 0-5% | 0-5% | 3-6% |
| W | 0-5% | 0-5% | 0-16% | 0-5% |
| Y | 0-5% | 0-5% | 0-5% | 0-5% |
| Zr | 0-5% | 0-20% | 0-5% | 0-5% |

| Component/ Wt. % | Ex. 183 | Ex. 184 | Ex. 185 | Ex. 186 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 1-15% | 2-10% | 3-8% | 0-5% |
| Nb | 0-5% | 0-5% | 0-5% | 20-45% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |

-continued

| | | | | |
|---|---|---|---|---|
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 1-15% |
| Tc | 0-5% | 0-5% | 0-5% | 0-5% |
| Ti | 51-70% | 51-70% | 55-70% | 51-70% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 20-40% | 22-38% | 27-33% | 1-15% |

| Component/ Wt. % | Ex. 187 | Ex. 188 | Ex. 189 | Ex. 190 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 25-40% | 30-40% | 25-40% | 26-32% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 2-8% | 3-6% | 5-15% | 10-14% |
| Tc | 0-5% | 0-5% | 0-5% | 0-5% |
| Ti | 51-70% | 52-63% | 51-68% | 51-62% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-12% | 4-8% | 2-8% | 2-6% |

| Component/ Wt. % | Ex. 191 | Ex. 192 | Ex. 193 | Ex. 194 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 5-35% | 10-30% | 15-25% |
| Cu | 0-5% | 0-5% | 0-5% | 0-5% |
| Co | 0-5% | 20-55% | 25-50% | 35-45% |
| Fe | 0-5% | 3-25% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 2-15% | 3-12% | 4-9% |
| Nb | 30-40% | 0-5% | 0-5% | 0-5% |
| Ni | 0-5% | 4-23% | 5-20% | 10-18% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 1-3% | 0-5% | 0-5% | 0-5% |
| Tc | 0-5% | 0-5% | 0-5% | 0-5% |
| Ti | 51-67% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-5% | 0-5% | 0-5% | 0-5% |

-continued

| Component/ Wt. % | Ex. 195 | Ex. 196 | Ex. 197 | Ex. 198 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 30-65% | 40-60% | 45-55% | 0-5% |
| Nb | 0-5% | 0-5% | 0-5% | 55-99.75% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 30-56% | 40-60% | 45-55% | 0.25-45% |

| Component/ Wt. % | Ex. 199 | Ex. 200 | Ex. 201 | Ex. 202 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 75-99.5% | 95-99.25% | 55-78.5% | 68-74.25% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 20-35% | 25-30% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 1-8% | 0-5% |
| Y | 0-5% | 0-5% | 0-5% | 0-5% |
| Zr | 0.5-25% | 0.75-5% | 0.5-5% | 0.75-3% |

| Element/ Wt. % | Ex. 203 | Ex. 204 | Ex. 205 | Ex. 206 |
|---|---|---|---|---|
| Re | 30-75% | 40-75% | 45-75% | 45-70% |
| Cr | 25-70% | 25-65% | 25-55% | 30-55% |
| Mo | 0-25% | 0-25% | 1-25% | 2-25% |
| Bi | 0-25% | 0-25% | 0-25% | 0-25% |
| Cr | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |

-continued

| | | | | |
|---|---|---|---|---|
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |
| C | <0.06 | <0.06 | <0.06 | <0.06 |
| N | <0.06 | <0.06 | <0.06 | <0.06 |
| O | <0.06 | <0.06 | <0.06 | <0.06 |

In Examples 1-206, it will be appreciated that all of the above ranges include any value between the range and any other range that is between the ranges set forth above. Any of the above values that include the ≤ symbol includes the range from 0 to the stated value and all values and ranges therebetween.

In accordance with another and/or alternative non-limiting aspect of the present disclosure, the weight percent of rhenium plus the weigh percent of the combined weight percentage of bismuth, niobium, tantalum, tungsten, titanium, vanadium, chromium, manganese, yttrium, zirconium, technetium, ruthenium, rhodium, hafnium, osmium, copper, and iridium in the metal alloy can be optionally greater than the weight percent of molybdenum. In one specific non-limiting formulation, the weight percent of rhenium plus the weight percent of the combined weight percentage of bismuth, chromium, iridium, niobium, tantalum, titanium, yttrium, and zirconium in the metal alloy is greater than the weight percent of molybdenum. In another specific non-limiting formulation, the weight percent of rhenium plus the weigh percent of the combined weight percentage of chromium, niobium, tantalum, and zirconium in the metal alloy is greater than the weight percent of molybdenum. In another specific non-limiting formulation, the weight percent of molybdenum in the metal alloy is at least 10 wt. % and less than 50 wt. % (and all values and ranges therebetween). In another specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of bismuth, niobium, tantalum, tungsten, titanium, vanadium, chromium, manganese, yttrium, zirconium, technetium, ruthenium, rhodium, hafnium, osmium, copper, and iridium in the metal alloy is 11-41 wt. % (and all values and ranges therebetween). In another specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of bismuth, chromium, iridium, niobium, tantalum, titanium, yttrium, and zirconium in the metal alloy is 11-41 wt. % (and all values and ranges therebetween). In another specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of chromium, niobium, tantalum, and zirconium in the metal alloy is 11-41 wt. % (and all values and ranges therebetween). In another specific non-limiting embodiment of the invention, the weight percent of rhenium in the metal alloy is greater than the combined weight percent of bismuth, chromium, iridium, niobium, tantalum, titanium, yttrium, and zirconium in the metal alloy. In another specific non-limiting formulation, the weight percent of rhenium in the metal alloy is greater than the combined weight percent of chromium, niobium, tantalum, and zirconium in the metal alloy.

In another and/or alternative non-limiting aspect of the present disclosure, the atomic weight percent of rhenium to the atomic weight percent of the combination of bismuth, niobium, tantalum, tungsten, titanium, vanadium, chromium, manganese, yttrium, zirconium, technetium, ruthenium, rhodium, hafnium, osmium, copper, and iridium can be optionally be 0.7:1 to 1.5:1 (and all values and ranges therebetween), typically 0.8:1 to 1.4:1, more typically 0.8:1 to 1.25:1, and still more typically about 0.9:1 to 1.1:1 (e.g., 1:1). In one specific non-limiting formulation, the atomic weight percent of rhenium to the atomic weight percent of the combination of bismuth, chromium, iridium, niobium, tantalum, titanium, yttrium, and zirconium is 0.7:1 to 5.1:1 (and all values and ranges therebetween), typically 0.8:1 to 1.5:1, more typically 0.8:1 to 1.25:1, and still more typically about 0.9:1 to 1.1:1 (e.g., 1:1). In one specific non-limiting formulation, the atomic weight percent of rhenium to the atomic weight percent of the combination of chromium, niobium, tantalum, and zirconium is 0.7:1 to 5.1:1 (and all values and ranges therebetween), typically 0.8:1 to 1.5:1, more typically 0.8:1 to 1.25:1, and still more typically about 0.9:1 to 1.1:1 (e.g., 1:1).

In another and/or alternative non-limiting aspect of the present disclosure, when the metal alloy includes two of bismuth, niobium, tantalum, tungsten, titanium, vanadium, chromium, manganese, yttrium, zirconium, technetium, ruthenium, rhodium, hafnium, osmium, copper, and iridium, the atomic ratio of the two metals can be optionally be 0.4:1 to 2.5:1 (and all values and ranges therebetween), and typically 0.5:1 to 2:1. In one specific non-limiting formulation, when the metal alloy includes two of bismuth, chromium, iridium, niobium, tantalum, titanium, yttrium, and zirconium, the atomic ratio of the two metals is 0.4:1 to 2.5:1 (and all values and ranges therebetween), and typically 0.5:1 to 2:1. In another specific non-limiting formulation, when the metal alloy includes two of chromium, niobium, tantalum, and zirconium, the atomic ratio of the two metals is 0.4:1 to 2.5:1 (and all values and ranges therebetween), and typically 0.5:1 to 2:1.

In another and/or alternative non-limiting aspect of the present disclosure, the metal alloy optionally includes less than about 5 wt. % (e.g., 0-4.999999 wt. % and all values and ranges therebetween) other metals and/or impurities, typically 0-1 wt. %, more typically 0-0.1 wt. %, even more typically 0-0.01 wt. %, and still even more typically 0-0.001 wt. %. A high purity level of the metal alloy results in the formation of a more homogeneous alloy, which in turn results in a more uniform density throughout the metal alloy, and also results in the desired yield and ultimate tensile strengths of the metal alloy. In one specific non-limiting formulation, the metal alloy is formed of rhenium plus at least two metals selected from the group of molybdenum, bismuth, niobium, tantalum, tungsten, titanium, vanadium, chromium, manganese, yttrium, zirconium, technetium, ruthenium, rhodium, hafnium, osmium, copper, and iridium, and the content of metal alloy that includes other elements and compounds is 0-0.1 wt. %, typically 0-0.01 wt. %, and more typically 0-0.001 wt. %. In another specific non-limiting formulation, the metal alloy is formed of rhenium plus at least two metals selected from the group of molybdenum, bismuth, chromium, iridium, niobium, tantalum, titanium, yttrium, and zirconium, and the content of metal alloy that includes other elements and compounds is 0-0.1 wt. %, typically 0-0.01 wt. %, and more typically 0-0.001 wt. %. In another specific non-limiting formulation, the metal alloy is formed of rhenium plus at least three metals selected from the group of rhenium, molybdenum, chromium, niobium, tantalum, and zirconium, and the content of metal alloy that includes other elements and compounds is 0-0.1 wt. %, typically 0-0.01 wt. %, and more typically 0-0.001 wt. %.

In another and/or alternative non-limiting aspect of the present disclosure, the cervical plate is made from a refractory metal alloy that allows the thickness of the cervical plate to be thinner than standard stainless steel, standard cobalt-chromium alloys, and standard titanium alloys. When the cervical plate is partially or fully formed of a refractory metal alloy, the mechanical characteristics of the cervical plate are superior to competitive products made of standard stainless steel, standard cobalt-chromium alloys, and standard titanium alloys. The superior mechanical characteristics of the cervical plate that includes refractory metal alloy can be used to form a cervical plate that is much narrower and/or thinner than cervical plates formed of standard stainless steel, standard cobalt-chromium alloys, and standard titanium alloys.

In another and/or alternative non-limiting aspect of the present disclosure, the use of refractory metal alloy or a metal alloy that includes at least 15 awt. % rhenium to at least partially form the cervical plate can thus 1) increase the radiopacity of the cervical plate, 2) increase the radial strength of the cervical plate, 3) increase the yield strength and/or ultimate tensile strength of the cervical plate, 4) improve the stress-strain properties of the cervical plate, 5) improve the strength and/or durability of the cervical plate, 6) increase the hardness of the cervical plate, 7) improve the biostability and/or biocompatibility properties of the cervical plate, 8) resist cracking in the cervical plate and resist propagation of cracks, 9) increase yield strength of the cervical plate, 10) improve durability of the cervical plate, 11) reduce adverse tissue reactions after implant of the cervical plate, 12) reduce metal ion release after implant of the cervical plate, 13) reduce corrosion of the cervical plate, 14) reduce allergic reaction after implant of the cervical plate, 15) improve hydrophilicity of the cervical plate, 16) improve ductility of the cervical plate, and/or 17) reduce toxicity of the cervical plate after implant of the cervical plate. The cervical plate generally includes one or more materials that impart the desired properties to the cervical plate to function properly and effectively and to withstand the manufacturing processes needed to produce the cervical plate. These manufacturing processes can include, but are not limited to, laser cutting, etching, annealing, drawing, pilgering, electroplating, electro-polishing, machining, plasma coating, 3D printed coatings, 3D printing, chemical vapor deposition, chemical polishing, cleaning, pickling, ion beam deposition or implantation, sputter coating, vacuum deposition, etc. In one non-limiting embodiment, at least a portion or all of the cervical plate is formed by a 3D printing process.

In another and/or alternative non-limiting aspect of the present disclosure, the metal alloy used to partially or fully form the cervical plate can be nitrided; however, this is not required. After the metal alloy is nitrided, the refractory metal alloy is typically cleaned; however, this is not required. During the nitriding process, the surface of the metal alloy is modified by the presence of nitrogen. The nitriding process can be by gas nitriding, salt bath nitriding, or plasma nitriding. In gas nitriding, the nitrogen diffuses onto the surface of the metal alloy, thereby creating a nitrided layer.

In yet another and/or alternative non-limiting aspect of the present disclosure, the cervical plate can include, contain, and/or be coated with one or more agents that facilitate in the success of the cervical plate and/or treated area. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to, viral, fungal, and/or bacterial infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; nerve repair; neural regeneration and/or the like. The type and/or amount of agent included in and/or coated on the cervical plate can vary. When two or more agents are included in and/or coated on the cervical plate, the amount of two or more agents can be the same or different. The type and/or amount of agent included on, in, and/or in conjunction with cervical plate are generally selected to address one or more clinical events. Typically, the amount of agent included on, in, and/or used in conjunction with the cervical plate is about 0.01-100 ug per $mm^2$ and/or at least about 0.00001 wt. % of device; however, other amounts can be used. In one non-limiting embodiment of the disclosure, the cervical plate can be partially or fully coated and/or impregnated with one or more agents to facilitate in the success of a particular medical procedure. The amount of the two of more agents on, in, and/or used in conjunction with the cervical plate can be the same or different. The one or more agents can be coated on and/or impregnated in the cervical plate by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition.

In a further and/or alternative non-limiting aspect of the present disclosure, the one or more agents on and/or in the cervical plate (when used) can be released in a controlled manner so the area to be treated is provided with the desired dosage of agent over a sustained period of time. As can be appreciated, controlled release of one or more agents on the cervical plate is not always required and/or desirable. As such, one or more of the agents on and/or in the cervical plate can be uncontrollably released from the cervical plate during and/or after insertion of the cervical plate in the treatment area. It can also be appreciated that one or more agents on and/or in the cervical plate can be controllably released from the cervical plate and one or more agents on and/or in the cervical plate can be uncontrollably released from the cervical plate. It can also be appreciated that one or more agents on and/or in one region of the cervical plate can be controllably released from the cervical plate and one or more agents on and/or in the cervical plate can be uncontrollably released from another region on the cervical plate. As such, the cervical plate can be designed such that 1) all the agent on and/or in the cervical plate is controllably released, 2) some of the agent on and/or in the cervical plate is controllably released and some of the agent on the cervical plate is non-controllably released, or 3) none of the agent on and/or in the cervical plate is controllably released. The cervical plate can also be designed such that the rate of release of the one or more agents from the cervical plate is the same or different. The cervical plate can also be designed such that the rate of release of the one or more agents from one or more regions on the cervical plate is the same or different. Non-limiting arrangements that can be used to control the release of one or more agents from the cervical plate include 1) at least partially coating one or more agents with one or more polymers, 2) at least partially incorporating and/or at least partially encapsulating one or more agents into and/or with one or more polymers, and/or 3) inserting one or more agents in pores, passageway, cavities, etc., in the cervical plate and at least partially coating or covering such pores, passageway, cavities, etc., with one or more polymers. As can be appreciated, other or additional arrangements can be used to control the release of one or more agents from the cervical plate.

In another and/or alternative non-limiting aspect of the present disclosure, the cervical plate, when including and/or coated with one or more agents, can include and/or be coated with one or more agents that are the same or different in different regions of the cervical plate and/or have differing amounts and/or concentrations in differing regions of the cervical plate. For instance, the cervical plate can be 1) coated with and/or include one or more biologicals on at least one portion of the cervical plate and at least another portion of the cervical plate is not coated with and/or includes agent; 2) coated with and/or include one or more biologicals on at least one portion of the cervical plate that is different from one or more biologicals on at least another portion of the cervical plate; and/or 3) coated with and/or include one or more biologicals at a concentration on at least one portion of the cervical plate that is different from the concentration of one or more biologicals on at least another portion of the cervical plate; etc.

In still yet another and/or alternative non-limiting aspect of the present disclosure, one or more portions of the cervical plate can 1) include the same or different agents, 2) include the same or different amount of one or more agents, 3) include the same or different polymer coatings, 4) include the same or different coating thicknesses of one or more polymer coatings, 5) have one or more portions of the cervical plate controllably release and/or uncontrollably release one or more agents, and/or 6) have one or more portions of the cervical plate controllably release one or more agents and one or more portions of the cervical plate uncontrollably release one or more agents.

In yet another and/or alternative non-limiting aspect of the disclosure, the cervical plate can include a marker material that facilitates enabling the cervical plate to be properly positioned in a body passageway. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.). In one non-limiting embodiment, the marker material is visible to x-rays (i.e., radiopaque). The marker material can form all or a portion of the cervical plate and/or be coated on one or more portions (flaring portion and/or body portion, at ends of cervical plate, at or near transition of body portion and flaring section, etc.) of the cervical plate. The location of the marker material can be on one or multiple locations on the cervical plate. The size of the one or more regions that include the marker material can be the same or different. The marker material can be spaced at defined distances from one another to form ruler-like markings on the cervical plate to facilitate in the positioning of the cervical plate in a body passageway.

The cervical plate can include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology.

The cervical plate can include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the cervical plate. As defined herein, a "micro-structure" is a structure that has at least one dimension (e.g., average width, average diameter, average height, average length, average depth, etc.) that is no more than about 2 mm, and typically no more than about 1 mm. As can be appreciated, when the cervical plate includes one or more surface structures, 1) all the surface structures can be micro-structures, 2) all the surface structures can be non-micro-structures, or 3) a portion of the surface structures can be micro-structures and a portion can be non-micro-structures. Non-limiting examples of structures that can be formed on the cervical plates are illustrated in United States Patent Publication Nos. 2004/0093076 and 2004/0093077, which are incorporated herein by reference.

In still yet another and/or alternative non-limiting aspect of the present disclosure, there is provided a near net process for a body or other metal component of the cervical plate. In one non-limiting embodiment of the disclosure, there is provided a method of powder pressing materials and increasing the strength post sintering by imparting additional cold work. In one non-limiting embodiment, the green part is pressed and then sintered. Thereafter, the sintered part is again pressed to increase its mechanical strength by imparting cold work into the pressed and sintered part. Generally, the temperature during the pressing process after the sintering process is 20-100° C. (and all values and ranges therebetween), typically 20-80° C., and more typically 20-40° C. As defined herein, cold working occurs at a temperature of no more than 150° C. (e.g., 10-150° C. and all values and ranges therebetween). The change in the shape of the repressed post-sintered part needs to be determined so the final part (pressed, sintered and re-pressed) meets the dimensional requirements of the final formed part. For a Mo47.5Re alloy, MoRe alloy, ReW alloy, molybdenum alloy, tungsten alloy, rhenium alloy, other type of refractory metal alloy, or TWIP alloy formed of a high titanium content, a prepress pressure of 1-300 tsi (1 ton per square inch) (and all values and ranges therebetween) can be used followed by a sintering process of at least 1600° C. (e.g., 1600-2600° C. and all values and ranges therebetween) and a post sintering press at a pressure of 1-300 tsi (and all values and ranges therebetween) at a temperature of at least 20° C. (e.g., 20-100° C. and all values and ranges therebetween; 20-40° C., etc.). There is also provided a process of increasing the mechanical strength of a pressed metal part by repressing the post-sintered part to add additional cold work into the material, thereby increasing its mechanical strength. There is also provided a process of powder pressing to a near net or final part using metal powder. In one non-limiting embodiment, the metal powder used to form the near net or final part includes a minimum of 40% rhenium by weight and at least 30% molybdenum, and the remainder can optionally include one or more elements of tungsten, tantalum, zirconium, iridium, titanium, bismuth, and yttrium. In another non-limiting embodiment, the metal powder used to form the near net or final part includes 20-80 wt. % rhenium (and all values and ranges therebetween), 20-80 wt. % molybdenum (and all values and ranges therebetween), and optionally one or more elements of tungsten, tantalum, zirconium, iridium, titanium, bismuth, and yttrium. In another non-limiting embodiment, the metal powder used to form the near net or final part includes tungsten (20-60 wt. % and all values and ranges therebetween), rhenium (20-80 wt. % and all values and ranges therebetween) and one or more other elements 0-5 wt. % (and all values and ranges therebetween). In another non-limiting embodiment, the metal powder used to form the near net or final part includes tungsten (20-80 wt. % and all values and ranges therebetween), rhenium (20-80 wt. % and all values and ranges therebetween), molybdenum (0-15 wt. % and all values and ranges therebetween), and one or more other elements 0-5 wt. % (and all values and ranges therebetween). In another non-limiting embodiment, the metal powder used to form the near net or final part includes tungsten (20-80 wt. % and all values and ranges therebetween), copper (1-30 wt. % and all values and ranges therebetween), and one or more other elements 0-5 wt. % (and all values and ranges therebetween). In another non-limiting embodiment, the metal powder used to form the near net or final part includes a titanium alloy or a cobalt alloy. The ductility of the refractory metal alloy measured as % reduction in area can increase and yield and ultimate tensile strength can increase.

In one non-limiting object of the present disclosure, there is the provision of a cervical plate for use as a spinal implant comprising a body that has a plurality of openings therethrough and a variable cross-sectional area along a longitudinal length of the cervical plate.

In another and/or alternative non-limiting object of the present disclosure, there is the provision of a cervical plate for use as a spinal implant comprising a body that has a plurality of openings therethrough, and wherein a maximum cross-sectional area in a region of the body of the cervical plate that is widest is greater than a maximum cross-sectional area in a region of the body of the cervical plate that is narrowest.

In another and/or alternative non-limiting object of the present disclosure, there is the provision of a cervical plate for use as a spinal implant wherein a cross-sectional area in a region of the body of the cervical plate that is widest is 10-40% greater than the cross-sectional area in a region of the body of the cervical plate that is narrowest.

In another and/or alternative non-limiting object of the present disclosure, there is the provision of a cervical plate for use as a spinal implant wherein the body is at least partially formed of a refractory alloy.

In another and/or alternative non-limiting object of the present disclosure, there is the provision of a cervical plate for use as a spinal implant wherein an angle of a screw set in the screw opening to the top surface of the cervical plate is 0-25° relative to a central longitudinal axis of the screw opening.

In another and/or alternative non-limiting object of the present disclosure, there is the provision of a cervical plate for use as a spinal implant wherein two or more screw openings are configured to cause the angle of the screw set in the screw openings to be different from one another.

In another and/or alternative non-limiting object of the present disclosure, there is the provision of a cervical plate for use as a spinal implant wherein the cervical plate includes at least one cam recess that is configured to releasably engage a cam; a portion of the cam recess includes a cam opening that passes fully through the cervical plate; 10-50% of said cam recess does not fully penetrate the cervical plate; a portion of the cam recess that does not fully penetrate the cervical plate is recessed from the top surface of the cervical plate; the cam recess is spaced from the outer peripheral edge of the cervical plate.

In another and/or alternative non-limiting object of the present disclosure, there is the provision of a cervical plate for use as a spinal implant wherein a portion of the cam recess terminates at at least one screw opening that is located adjacent to the cam recess.

In another and/or alternative non-limiting object of the present disclosure, there is the provision of a cervical plate for use as a spinal implant wherein the cam recess includes a sloped surface positioned between two of said screw openings that are located adjacent to the cam recess; the slope surface is configured and oriented so said slope surface does not engage a cam during rotation of a cam in the cam recess.

In another and/or alternative non-limiting object of the present disclosure, there is the provision of a cervical plate for use as a spinal implant wherein the cam recess includes one or more cam stops to limit rotation of a cam in the cam recess.

In another and/or alternative non-limiting object of the present disclosure, there is the provision of a cervical plate for use as a spinal implant wherein the cervical plate includes one or more undulations on an outer side peripheral edge of the cervical plate.

In another and/or alternative non-limiting object of the present disclosure, there is the provision of a cervical plate for use as a spinal implant wherein the screw openings allow for dual angulation of a screw in the screw opening along a longitudinal axis of the cervical plate and along a lateral axis of the cervical plate.

In another and/or alternative non-limiting object of the present disclosure, there is the provision of a cervical plate for use as a spinal implant wherein one or more of the screw openings includes one or more concavely indented surfaces; the concavely indented surfaces extend into the screw openings; and the concavely indented surfaces are not threaded surfaces.

These and other objects and advantages will become apparent from the discussion of the distinction between the disclosure and the prior art and when considering the non-limiting embodiment illustrated in the accompanying drawings.

BRIEF DESCRIPTION OF THE DRAWINGS

The above and other features and advantages of the disclosure will become apparent from a consideration of the subsequent detailed description presented in connection with the accompanying drawings in which.

DETAILED DESCRIPTION OF VARIOUS NON-EMBODIMENTS OF DISCLOSURE

Figure 1:
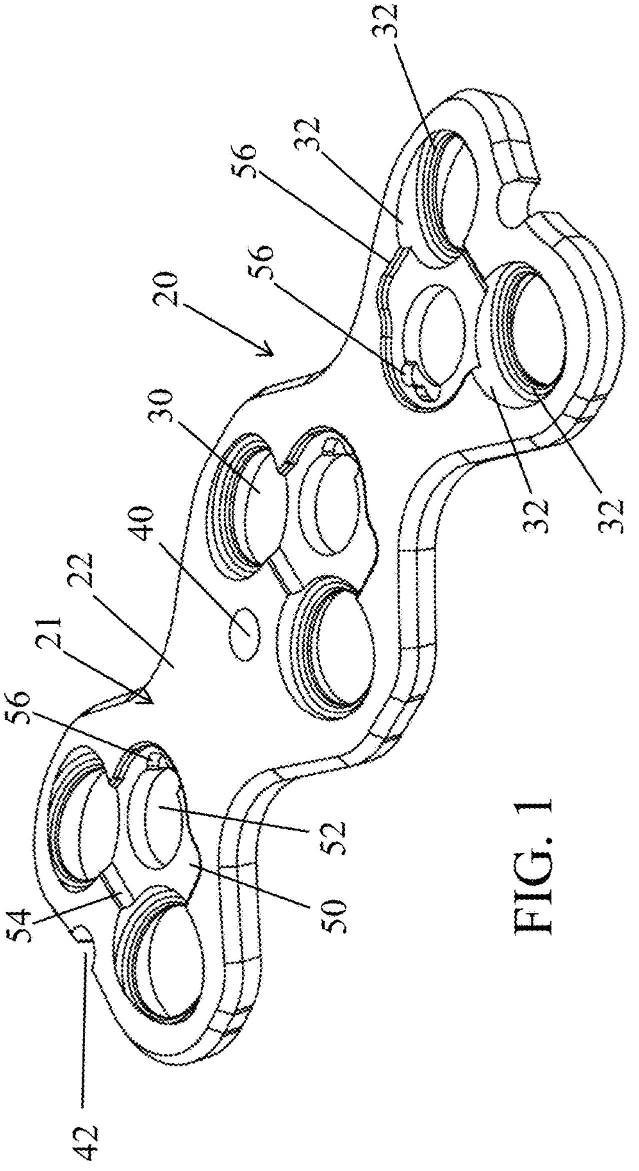
FIG. 1 is a side elevation view of a Cervical Plate in accordance with the new design.

A more complete understanding of the articles/devices, processes and components disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g. "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Referring now to the drawings, FIGS. 1-18 illustrate a cervical plate assembly 10 that includes a cervical plate 20 made in accordance with the present disclosure. In one non-limiting configuration, the cervical plate 20 can be configured and dimensioned for attachment on the anterior portion of a cervical spine (not shown). The cervical plate 20 can be manufactured from any suitable biocompatible material, including metal, such as titanium, stainless steel, cobalt-chromium-molybdenum alloy, titanium-aluminum vanadium alloy, molybdenum titanium alloy, molybdenum rhenium alloy, molybdenum alloy, rhenium alloy, rhenium-chromium alloy, a rhenium containing metal alloy (e.g., metal alloy that includes at least 15 awt. % rhenium), or other suitable metallic alloys.

The cervical plate 10 is configured to provide a bone fixation assembly that can accept and fix fasteners 100 (e.g., screws, etc.).

Figure 2:
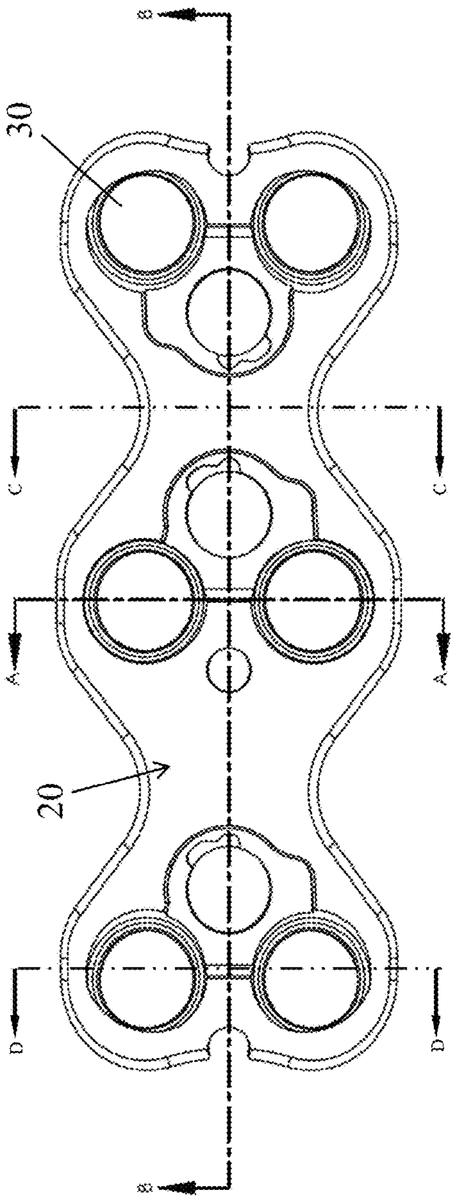
FIG. 2 is a top plan view of the Cervical Plate of FIG. 1.
Figure 3:
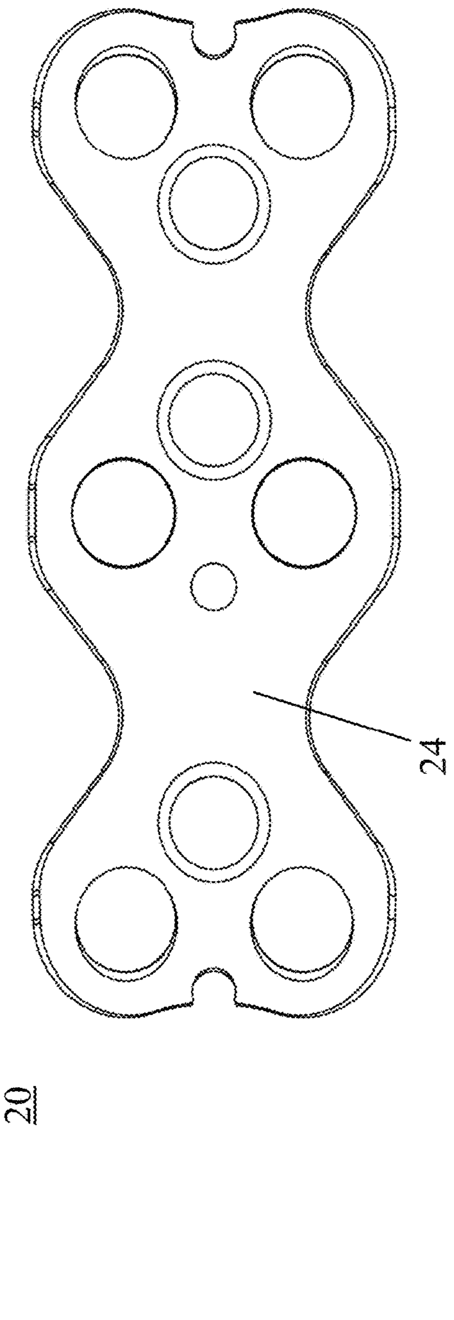
FIG. 3 is a bottom plan view of the Cervical Plate of FIG. 1.
Figure 4:
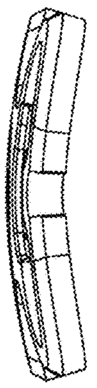
FIG. 4 is a front plan view of the Cervical Plate of FIG. 1.
Figure 5:
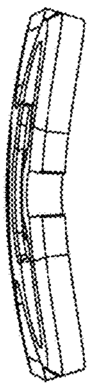
FIG. 5 is a rear plan view of the Cervical Plate of FIG. 1.
Figure 6:
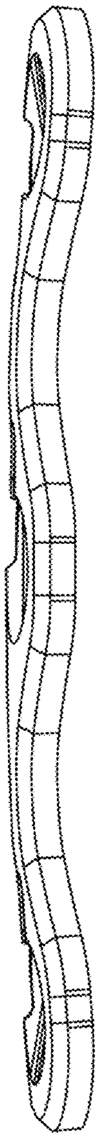
FIG. 6 is a side plan view of the Cervical Plate of FIG. 1.
Figure 7:
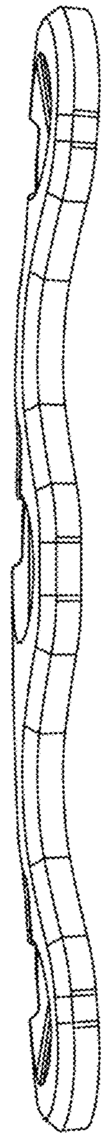
FIG. 7 is an opposite side plan view of the Cervical Plate of FIG. 1.
Figure 8:
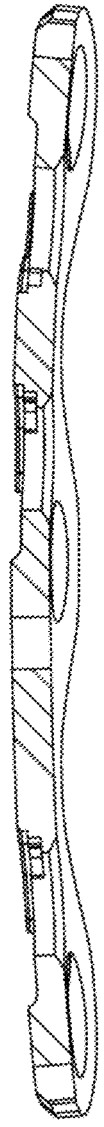
FIG. 8 is a cross-sectional view along lines B-B of FIG. 2.

Cervical plate 20 has a body 21 that has a lower surface 24 and an upper surface 22 and one or more screw openings 30 that extend from the upper surface 22 to the lower surface 24. Cervical plate 20 also includes a smaller tool opening 40 and end indents 42 that pass fully through the cervical plate. One or more tool openings 40 and one or more end indents 42 can be used by a physician to orient cervical plate 20 in position relative to the spine using various type of instruments and tools (not shown). The size, shape, and/or configuration of one or more tool openings 40 and one or more end indents 42 are non-limiting. As illustrated in FIGS. 1-3, tool opening 40 has a smaller diameter (e.g., 5-80% smaller in diameter and all values and ranges therebetween) than the diameter of screw openings 30. As illustrated in FIGS. 1-3, the radius of the one or more end indents 42 has a smaller radius (e.g., 5-80% smaller in radius and all values and ranges therebetween) than the radius of screw openings 30. The one or more end indents 42 are illustrated as being located at one or both ends of cervical plate 20 (e.g., generally about the mid-end of cervical plate 20). It will be appreciated that more than two or less than two end indents 42 can be used and one or more end indents 42 can be located in additional or different locations on cervical plate 20. At least one of tool openings 40 is generally located in the mid-region of cervical plate 20 and spaced form the side edges of cervical plate 20. It will be appreciated that more than one tool opening 40 can be used and one or more tool openings 40 can be located in additional or different locations on cervical plate 20.

In one non-limiting embodiment, tool openings 40 are a circular or generally circular opening and have a maximum diameter of 1-4 mm (and all values and ranges therebetween, and typically 1.5-2.5 mm. Generally, the cross-sectional area of tool openings 40 is less than the openings in cam recesses 50 and screw openings 30. Generally, tool openings 40 are spaced from the outer perimeter of cervical plate 20 and also spaced from screw openings 30 and cam recesses 50.

Figure 17:
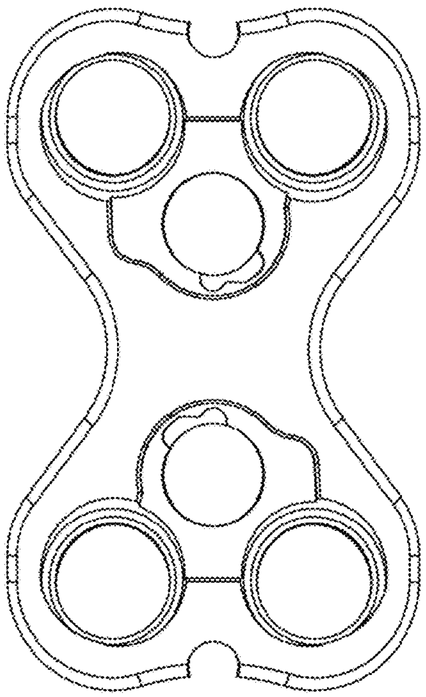
FIG. 17 is a top plan view of another non-limiting the Cervical Plate in accordance with the present disclosure.
Figure 18:
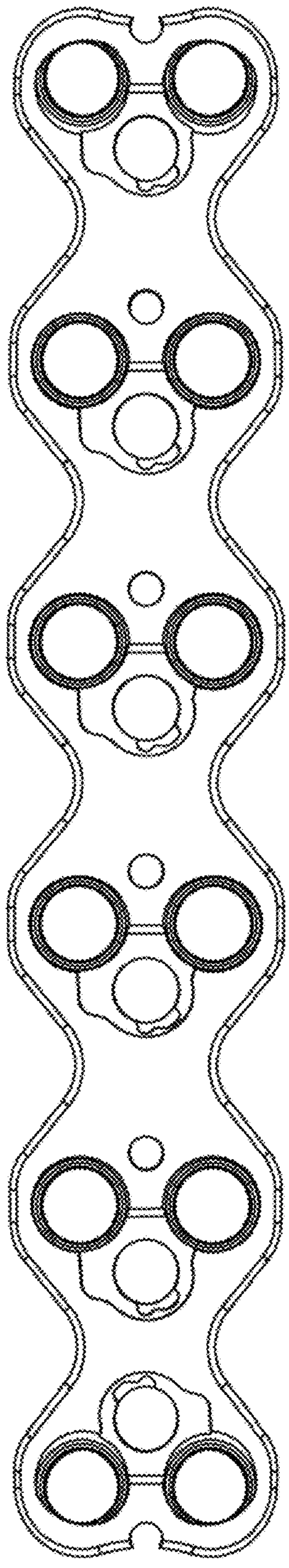
FIG. 18 is a top plan view of another non-limiting the Cervical Plate in accordance with the present disclosure.

As illustrated in FIGS. 1-2, top surface 22 of cervical plate 20 includes three cam recesses 50 that are configured to receive a cam (not shown) that can be releasably connected to top surface 22 of cervical plate 20. The number of cam recesses 50 on he cervical plate 20 and the shape, size, and/or configuration of cam recess 50 on cervical plate 20 are non-limiting. For example. FIG. 17 illustrates cervical plate 20 including two earn recesses 50, and FIG. 18 illustrates a cervical plate 20 including six cam recesses 50. Generally, cervical plate 20 includes 2-8 cam recesses 50.

Each of cam recesses 50 includes a cam opening 52. As illustrated in FIGS. 1, 2, 17 and 18, the cross-sectional area of can opening 52 is less than the cross-sectional area of cam recesses 50 (e.g., the cross-sectional area of the cam opening 52 is 5-70% less and all values and ranges therebetween of the cross-sectional area of cam recesses 50). In one non-limiting embodiment, a non-limiting size of cam opening 52 can be 2-6 mm (and all values and ranges therebetween), and typically about 3.8-4.2 mm. Cam opening 52 is generally spaced from the side edges of cam recesses 50. The general shape of cam opening 52 is generally circular. The shape and size of each of cam recess 50 is non-limiting. Cam openings 52 in cam recesses 50 are generally spaced from screw openings 30 and the outer perimeter of cervical plate 20. One or more of cam recesses 50 can border with or terminate at one or more of screw openings 30 as illustrated in FIGS. 1, 2, 17 and 18. Cam opening 52 is generally spaced an equal distance from the two adjacently positioned screw openings 30 as illustrated in FIGS. 1, 2, 17 and 18. As illustrated in FIGS. 1, 2, 17 and 18, the cross-sectional area of cam opening 52 is less than the cross-sectional area of the screw openings 30 (e.g., the cross-sectional area of cam opening 52 is 5-50% less and all values and ranges therebetween of the cross-sectional area of screw openings 30). As illustrated in FIGS. 1, 2 and 18, the cross-sectional area of cam opening 52 is greater than the cross-sectional area the tool opening 40 (e.g., the cross-sectional area of cam opening 52 is 10-200% greater and all values and ranges therebetween of the cross-sectional area of tool openings 40).

Cervical plate 20 in accordance with the present disclosure can be curved, contoured, straight, flat, undulating, etc. The cervical plate can be a periarticular plate or a straight plate. The cervical plate can be shaped to match a particular spinal bone surface to be treated.

The one or more screw openings 30 in cervical plate 20 are shown having a central axis X as illustrated in FIGS. 12-16, and are adapted to receive a fastener system 100.

Fastener system 100 can be any typical, standard locking fastener or a non-locking fastener system. Fastener system 100, such as a screw, includes a body 120 that optionally includes threads 122 or other arrangement on at least a portion of body 120. For example, body 120 can be fully threaded, partially threaded, comprise a helical blade, and/or may comprise one or more tacks, deployable talons, expanding elements, or so forth. As can be appreciated, body 120 of fastener system 100 can be a peg or pin shape. The end of body 120 can optionally include a self-tapping or self-drilling tip (not shown); however, this is not required. The screw can be optionally formed of a refractory metal alloy and/or a metal ally that includes at least 15 awt. % rhenium.

Fastener system 100 can include a head portion 110. Generally, the cross-section size of head portion 110 is greater than body 120. The shape of head portion 110 is non-limiting. The cross-sectional shape of the top region of head portion 110 is generally circular shaped; however, other shapes can be used. Head portion 110 can optionally include a cavity 112 to facilitate in inserting fastener system 100 into a bone and securing the cervical plate to the bone. The configuration of cavity 112 is non-limiting. Generally, cavity 112 is specially shaped to receive a tool to rotate and/or otherwise cause fastener system 110 to be inserted into a bone. Non-limiting shapes that can be used in cavity 112 include one or more dimples, ridges, bumps, textured areas, star shaped, polygonal shaped, or any other surface or shape. As can be appreciated, cavity 112 can include a threaded inner surface and a circular-cross-sectional shape.

As can be appreciated, the configuration of fastener system 100 is non-limiting. Many different configurations of head portion 110 and body portion 120 of fastener system 100 can be used with cervical plate 20 in accordance with the present disclosure. Generally the maximum cross-sectional area of head portion 110 is greater than the maximum cross-sectional area of screw openings 30 to prevent head portion 110 from fully passing through screw openings 30 when securing cervical plate 20 to a bone.

As illustrated in FIGS. 2, 17 and 18, screw openings 30 have a generally circular cross-sectional shape. In one non-limiting embodiment, the diameter of the one or more screw openings is 3-6 mm (and all values and ranges therebetween), and typically 4-5 mm. It will be appreciated that the screw openings 30 can have other cross-sectional shapes (e.g., oval, square, polygonal, etc.) and diameters. The spacing of two adjacently positioned screw openings 30 is generally 1.5-4.5 mm (and all values and ranges therebetween), and typically 2.5-4 mm. As illustrated in FIGS. 2, 17 and 18, screw openings 30 are spaced from the outer perimeter of cervical plate 20. In one non-limiting embodiment, two adjacently positioned screw openings 30 are spaced from the longitudinal central axis of cervical plate 20, and are positioned along the same lateral axis of the of cervical plate 20. Generally, the two adjacently positioned screw openings 30 are spaced generally an equal distance (e.g., ±0-5% and all values and ranges therebetween)) from the longitudinal central axis of cervical plate 20. As illustrated in FIGS. 2, 17 and 18, cam opening 52, the one or more tool openings 40, and/or one or more end indents 42 intersect the longitudinal central axis of cervical plate 20.

The top region of the inner surface of one or more screw openings 30 optionally has one or more concavely indented surfaces 32. Concavely indented surfaces 32 extend into screw openings 30. Concavely indented surfaces 32 can optionally be smooth and non-threaded. Such an arrangement can be used to form a non-locking arrangement for fastener system 100 with cervical plate 20. In one non-limiting arrangement, there is no thread to thread contact between the head of fastener system 100 with cervical plate 20 when the fastener system is fully connected to the bone. One non-limiting purpose of concavely indented surfaces 32 is to orient the longitudinal axis of fastener system 100 at a particular angle relative to body 21 of cervical plate 20 when body portion 120 of fastener system 100 in inserted into screw openings 30 during the securing of cervical plate 20 to the spine. Head portion 110 of fastener system 100 is configured to engage one or more concavely indented surfaces 32 can cause the central longitudinal axis of fastener system 100 to be oriented a) normal (e.g., 90°) to top surface 22 of body 21 of cervical plate 20 when fastener system 100 is fully inserted into screw openings 30 during the securing of cervical plate 20 to the spine, or b) a some angle from normal (e.g., 0.001°-30° and all values and ranges therebetween) to top surface 22 of body 21 of cervical plate 20 when fastener system 100 is fully inserted into screw openings 30 when securing of cervical plate 20 to the spine.

Concavely indented surfaces 32 can be formed of one or more partially circular or arcuate recess regions. Concavely indented surfaces 32 can be formed by a cutting process, stamping process, 3D printer, molding process, etc. The radius of curvature of the partially circular or arcuate recess regions is non-limiting. The depth of the partially circular or arcuate recess regions is less than the thickness of cervical plate 20. As can be appreciated, the size, shape, and configuration of concavely indented surfaces 32 in one or more of screw openings 30 are non-limiting.

Figure 12:
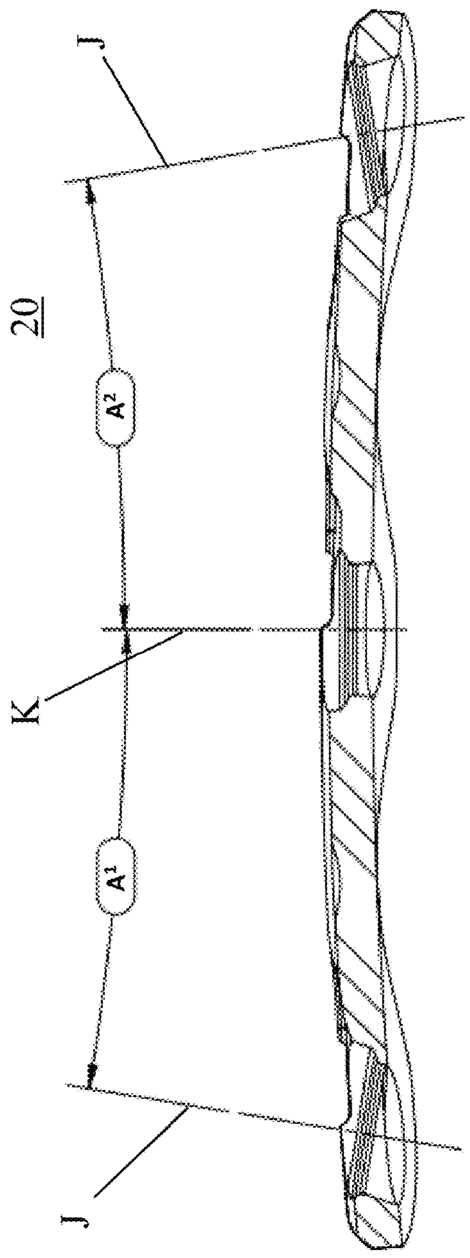
FIGS. 12-13 illustrate non-limiting dimensions of the axial orientation of the openings in the Cervical Plate.
Figure 13:
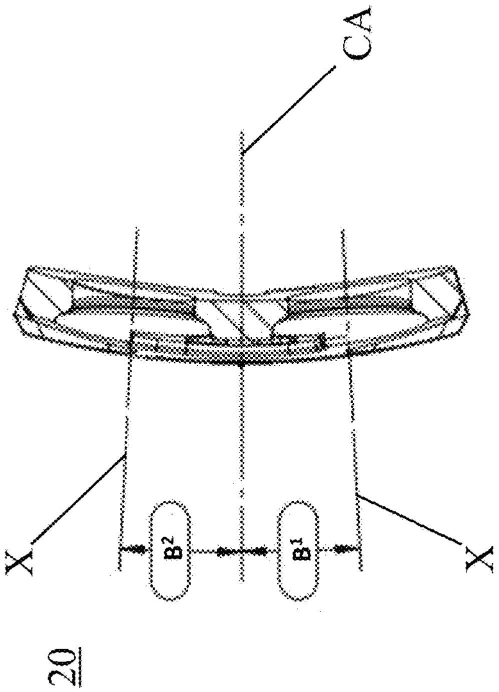
Figure 14:
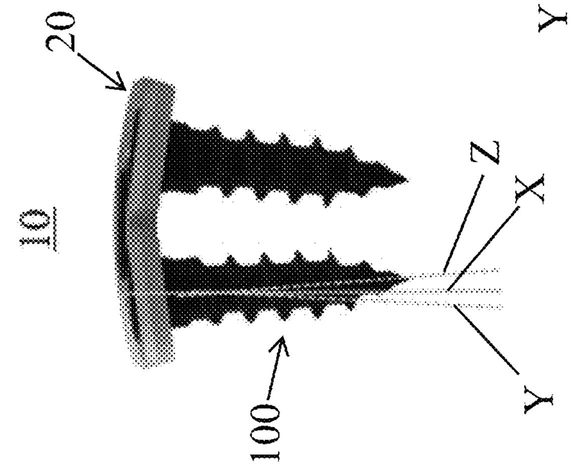
FIGS. 14-16 illustrated various non-limiting fastener or screw orientations that can be used to fasten the Cervical Plate to a body structure.
Figure 15:
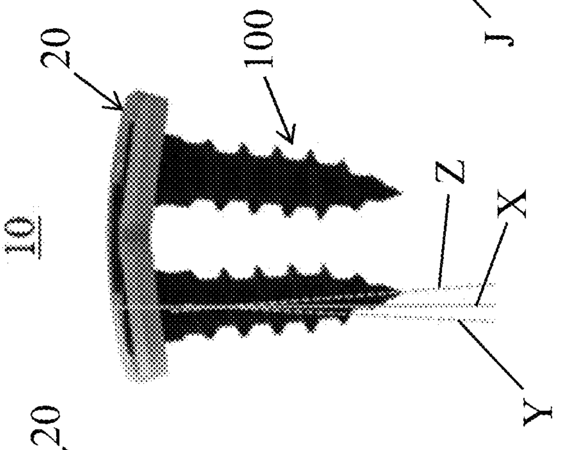
Figure 16:
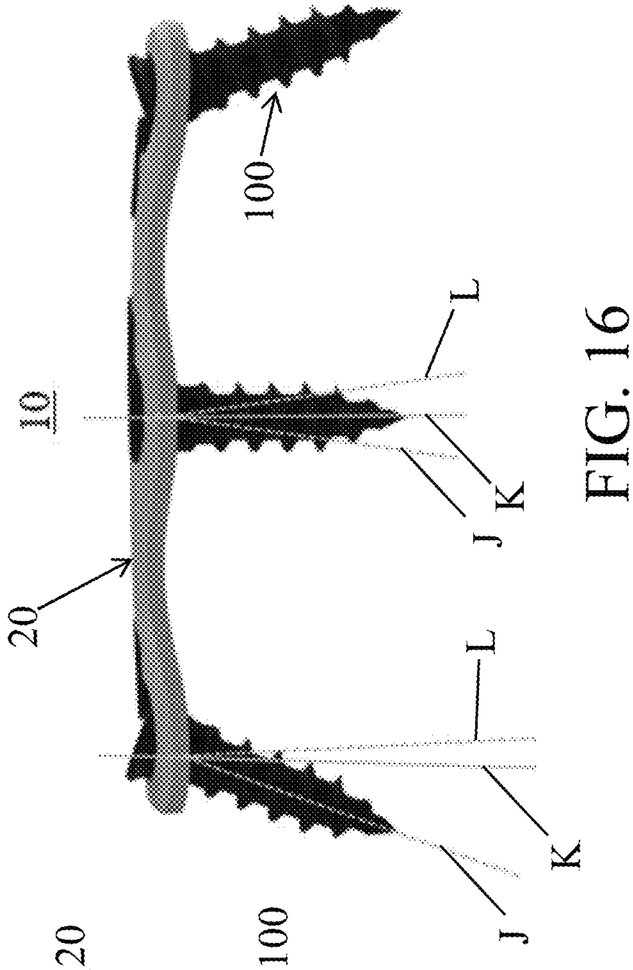

Referring now to FIGS. 12-16, screw openings 30 and concavely indented surfaces 32 in screw openings 30 can be selected to enable the central longitudinal axis of fastener system 100 to be oriented in screw opening 30 at various angles to the longitudinal axis of screw opening 30 when viewed from either the lateral or longitudinal axis of cervical plate 20. FIGS. 13-15 illustrate the central longitudinal axis of screw openings 30 and/or fastener system 100 along the lateral axis of cervical plate 20 as viewed from the end of cervical plate 20, and FIGS. 12 and 16 illustrate the central longitudinal axis of screw openings 30 and/or fastener system 100 along the longitudinal axis of cervical plate 20 as viewed from the side of the cervical plate.

Referring now to FIGS. 13, 14 and 15, the longitudinal axis line X represents the central longitudinal axis of screw opening 30 that is normal to top surface 22 of body 21 of cervical plate 20 along the lateral axis of cervical plate 20. The longitudinal axis line CA represents the central longitudinal axis of cervical plate 20 along the longitudinal central axis of cervical plate 20. The dashed longitudinal axis lines Y and Z represent a longitudinal axis through screw opening 30 that is not normal to the top surface 22 of the body 21 of cervical plate 20 when viewed along the lateral axis of cervical plate 20. For example, FIG. 14 illustrates that the central longitudinal axis of fastener system 100 is oriented along longitudinal axis Z that is oriented inwardly at an angle of about 0.50 to 8° from longitudinal axis line X. Longitudinal axis Y that is oriented outwardly at an angle of about −0.5-8° from longitudinal axis line X. Concavely indented surfaces 32 in screw opening 30 are configured to enable the central longitudinal axis of fastener system 100 to be oriented in screw opening 30 at an angle of −8-8° relative to central longitudinal axis X of screw opening 30.

As illustrated in FIG. 13, central longitudinal axis X of screw opening 30 along the lateral axis of cervical plate 20 as viewed from the end of cervical plate 20 are at a non-parallel angles $B^1$ and $B^2$ to longitudinal axis line CA of cervical plate 20. The end profile of cervical plate 20 illustrates a curved profile that results in central longitudinal axis X of screw opening 30 being non-parallel to longitudinal axis line CA of cervical plate 20. The angle of curvature is generally 0.1-10° (and all values and ranges therebetween). For example, if the angle of curvature of cervical plate 20 along the lateral axis of cervical plate 20 is 3.1°, then angles $B^1$ and $B^2$ would also be about 3.1°.

Referring to FIG. 16, the solid longitudinal axis line K represents the central longitudinal axis of screw opening 30 that is normal to top surface 22 of body 21 of cervical plate 20 along the longitudinal axis of cervical plate 20 when viewed from the side of cervical plate 20. The dashed longitudinal axis lines J and L represent a longitudinal axis through screw opening 30 that is not normal to top surface 22 of body 21 of cervical plate 20 along the longitudinal axis of cervical plate 20 when viewed from the side of cervical plate 20. The central longitudinal axis of fastener system 100 is oriented along longitudinal axis J which is oriented outwardly at an angle of about −10-−25° from longitudinal axis line K. Longitudinal axis L is oriented inwardly at an angle of about 0.5-6° from longitudinal axis line K. Concavely indented surfaces 32 in screw opening 30 is configured to enable the central longitudinal axis of fastener system 100 to be oriented in screw opening 30 at an angle of −25-6° relative to central longitudinal axis K of screw opening 30.

As illustrated in FIGS. 14 and 15, the majority (e.g., 51-100% and all values and ranges therebetween) of the top surface of head portion 110 of fastener system 100 is positioned level with or below top surface 22 of body 21 of cervical plate 20. As illustrated in FIG. 16, when the central longitudinal axis of fastener system 100 is oriented at an extreme angle (e.g., greater than +8° from longitudinal axis X, 25-90% (and all values and ranges therebetween)); the top surface of head portion 110 of fastener system 100 is positioned above top surface 22 of body 21 of cervical plate 20. However, in all of fastener system 100 orientations illustrated in FIGS. 14-16 and described above, concavely indented surfaces 32 in screw opening 30 are configured such that a least a portion of head portion 110 of fastener system 100 is seated in concavely indented surfaces 32 in screw opening 30 to form a stable and rigid connection between fastener system 100 and cervical plate 20 when fastener system 100 is fully inserted into screw openings 30 during the securing cervical plate 20 to the spine. In one non-limiting embodiment, 80-100% of the top surface of head portion 110 of fastener system 100 is positioned level with or below top surface 22 of body 21 of cervical plate 20 when fastener system 100 is fully inserted into screw openings 30 located inwardly from screw openings 30 located at each end of cervical plate 20. In one non-limiting embodiment, 5-70% of the top surface of head portion 110 of fastener system 100 is positioned above top surface 22 of body 21 of cervical plate 20 when fastener system 100 is fully inserted into screw openings 30 located at each end of cervical plate 20.

Referring again to FIGS. 12, 17 and 18, the longitudinal central axis of concavely indented surfaces 32 in screw opening 30 can have the same or different longitudinal central axis as screw opening 30. As illustrated in FIG. 12, the longitudinal central axis of concavely indented surfaces 32 in center screw opening 30 is the same or substantially the same (e.g. ±0-3°) as longitudinal central axis K of center screw opening 30. As also illustrated in FIG. 12, longitudinal central axis J of concavely indented surfaces 32 in screw openings 30 on the left and right sides of center screw opening 30 are not aligned with the longitudinal central axis of center screw opening 30. In one non-limiting embodiment, longitudinal central axis J of concavely indented surfaces 32 in screw openings 30 on the left and right sides of center screw opening 30 have an angle $A^1$ and $A^2$ that is 3-25° (and all values and ranges therebetween) from the central axis of screw openings 30 on the left and right sides of center screw opening 30. In another non-limiting embodiment, concavely indented surfaces 32 in screw openings 30 on one or both ends of cervical plate 20 have a longitudinal central axis that is not aligned with the longitudinal central axis of screw openings 30. In another non-limiting embodiment, one or more or all of longitudinal central axis of concavely indented surfaces 32 in screw openings 30 that are positioned inwardly of screw openings 30 that are positioned on the ends of cervical plate 20 have a longitudinal central axis that is aligned with the longitudinal central axis of screw openings 30.

As discussed above with regard to FIG. 16, the longitudinal central axis of fastener system 100 (when viewed from the side of cervical plate 20) when fully inserted into screw openings 30 may or may not be aligned with a) the longitudinal central axis of concavely indented surfaces 32 in the screw opening, and/or b) the longitudinal central axis of screw opening 30. As illustrated in FIG. 16, the longitudinal central axis of fastener system 100 in central screw openings 30 is illustrated as both aligned with the longitudinal central axis of concavely indented surfaces 32 in the screw opening 30, and the longitudinal central axis of screw opening 30. As also illustrated in FIG. 16, the longitudinal central axis of the fastener system 100 in screw openings 30 located at each end of cervical plate 20 are illustrated as aligned with the longitudinal central axis of concavely indented surfaces 32 in screw opening 30, but not aligned with the longitudinal central axis of screw opening 30. FIG. 16 further illustrates that the longitudinal central axis of fastener system 100 in each screw openings 30 can be adjusted as required.

Referring again to FIG. 12, the central longitudinal central axis of concavely indented surfaces 32 in central screw opening 30 (which is spaced inwardly of screw openings 30 that are located at the two ends of cervical plate 20) is the same or substantially the same as the longitudinal central axis central screw opening 30, and the central longitudinal central axis of concavely indented surfaces 32 in screw openings 30 on each end of cervical plate 20 have a longitudinal central axis that is not aligned with the longitudinal central axis of screw openings 30.

Referring to FIG. 17, cervical plate 20 only includes two sets of screw openings 30 that are positioned at each end of cervical plate 20. As such, since screw openings 30 are located at the ends of cervical plate 20, the central longitudinal central axis of concavely indented surfaces 32 in the two sets of screw openings 30 have a longitudinal central axis that is not aligned with the longitudinal central axis of screw openings 30.

Referring to FIG. 18, cervical plate 20 includes six sets of screw openings 30. The central longitudinal central axis of concavely indented surfaces 32 in the sets of screw openings 30 located at each end of cervical plate 20 have a longitudinal central axis that is not aligned with the longitudinal central axis of screw openings 30. The four sets of screw openings 30 that are located inwardly of screw openings 30 that are located at each end of cervical plate 20 have concavely indented surfaces 32 that have a longitudinal central axis that is aligned with the longitudinal central axis of screw openings 30.

As illustrated in FIGS. 12-16, the central longitudinal axis of fastener system 100 can be oriented at different angles relative to the central longitudinal axis of concavely indented surfaces 32 and/or screw opening 30 depending on the view from the lateral or longitudinal axis of cervical plate 20.

The number of screw openings 30 in cervical plate 20 is non-limiting. The shape, length, width, and/or thickness of cervical plate 20 is non-limiting.

As illustrated in FIGS. 1-3, 17 and 18, each side of cervical plate 20 can optionally have multiple arcuate regions that create a generally wavy side or sinusoidal-shaped edges of cervical plate 20; however, it can be appreciated that such arcuate regions are not required. The radius of curvature of the wavy side edges is generally 5-10 mm (and all values and ranges therebetween), and typically 7-9 mm. Due to these arcuate regions, the width of cervical plate 20 varies along the longitudinal length the cervical plate. Generally, the location of screw openings 30 in cervical plate 20 represents a larger width region of cervical plate 20 than the regions absent screw openings 30. In one non-limiting embodiment, the maximum width of the cervical plate (as measured along the lateral axis of cervical plate 20) that includes one or more screw openings 30 is 20-60% greater (and all values and ranges therebetween) than the minimum width of cervical plate 20 at a location between two screw openings 30. For example, as illustrated in FIG. 2, the maximum width of cervical plate 20 is along cross-sectional line A-A and the minimum width of cervical plate 20 is along cross-sectional line C-C.

Figure 9:
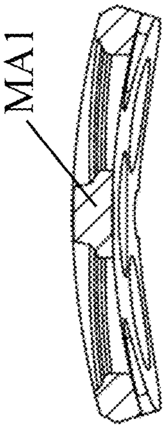
FIG. 9 is a cross-sectional view along lines A-A of FIG. 2.
Figure 10:
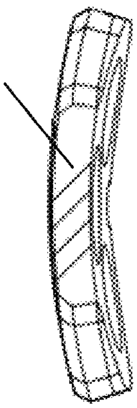
FIG. 10 is a cross-sectional view along lines C-C of FIG. 2.
Figure 11:
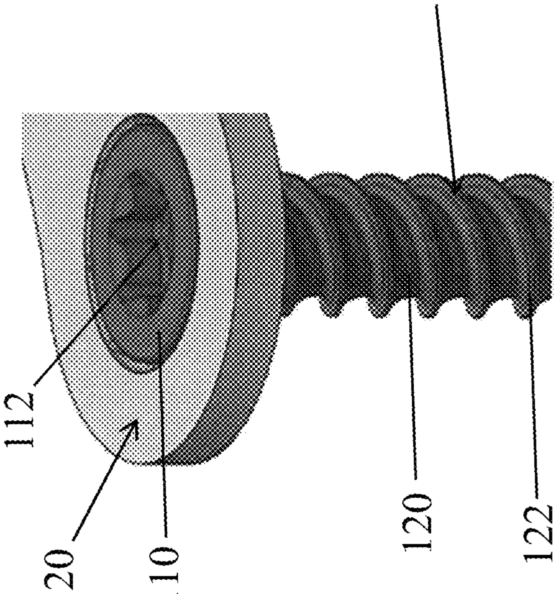
FIG. 11 illustrates a fastener inserted through a portion of the Cervical Plate.

As illustrated in FIGS. 9 and 10, the thickness of cervical plate 20 can vary along the longitudinal length of cervical plate 20. In one non-limiting configuration, the thickness of the cervical plate at the location of screw openings 30 is generally thicker than at the regions that are absent screw openings 30. For example, as illustrated in FIG. 9, the maximum cross-sectional area MA1 of the cervical plate at the location between screw openings 30 and at the central longitudinal axis of cervical plate 20 is greater (10-50% greater and all values and ranges therebetween) than the minimum cross-sectional area MA2 of cervical plate 20 that is not located between screw openings 30 and is located along the central longitudinal axis of cervical plate 20. For example, as illustrated in FIG. 2, maximum cross-sectional area MA1 of cervical plate is along cross-sectional line A-A at the central longitudinal axis of cervical plate 20 and the minimum width of cervical plate 20 is along cross-sectional line C-C at the central longitudinal axis of cervical plate 20.

In one specific non-limiting configuration of cervical plate 20, the cross-sectional area of the cervical plate along the longitudinal length of the cervical plate is 8-16 $mm^2$ (and all values and ranges therebetween); the cross-sectional area of the cervical plate optionally varies along the longitudinal length of the cervical plate; the maximum thickness of the cervical plate is 1-3 mm (and all values and ranges therebetween); the thickness of the cervical plate varies along the longitudinal length and/or latitudinal length of the cervical plate; the width of the cervical plate is 5-18 mm (and all values and ranges therebetween); and the width of the cervical plate varies along the longitudinal length of the cervical plate.

In another specific configuration of cervical plate 20, the cross-sectional area of the cervical plate along the longitudinal length of the cervical plate is 8.5-14 $mm^2$; the cross-sectional area of the cervical plate optionally varies along the longitudinal length of the cervical plate; the maximum thickness of the cervical plate is 1-3 mm; the thickness of the cervical plate varies along the longitudinal length and/or latitudinal length of the cervical plate; the width of the cervical plate is 7-17 mm; and the width of the cervical plate varies along the longitudinal length of the cervical plate; the maximum cross-sectional area and/or the thickness of the cervical plate at and/or about the region of the screw openings is greater than the minimum cross-sectional area and/or thickness of the cervical plate in the region of the cervical plate that is absent the screw openings and located between two sets of screw openings; the maximum cross-sectional area of the cervical plate at and/or about the region between of the screw openings of a set of screw openings is 10-14 $mm^2$, the minimum cross-sectional area of the cervical plate is 8.5-11 $mm^2$; the width of the cervical plate at and/or about the region of the screw openings is greater than the width of the cervical plate that is absent the screw openings; the maximum width of the cervical plate at and/or about the region of the screw openings is 10-17 mm; and the minimum width of the cervical plate is 7-9.5 mm.

In another specific configuration of cervical plate 20, the maximum width of the cervical plate along the longitudinal axis of the cervical plate is 14-16.5 mm and the minimum width along the longitudinal axis of the cervical plate is 7.2-8.5 mm.

As illustrated in FIGS. 2 and 18, when cervical plate 20 includes three of more sets of screw openings, the maximum width of the cervical plate at the location of the screw openings at the ends of the cervical plate is less (e.g., 5-20% and all values and ranges therebetween) than the maximum width of the cervical plate at the location of the screw openings that are spaced inwardly from the screw openings located at the ends of the cervical plate. For example, as illustrated in FIG. 2, the maximum width of the cervical plate along line A-A is greater than the maximum width of the cervical plate along line D-D. When the cervical plate includes two of more sets of screw openings located between the screw openings located at each end of the cervical plate, the maximum width of the cervical plate at the two of more sets of screw openings located between the screw openings located at each end of the cervical plate can be the same.

In another specific configuration, the width of each of the screw openings is 3.5-5 mm (and all values and ranges therebetween).

In another specific configuration, the distance between each of the screw openings is from the outer peripheral edge of the cervical plate is 1.2-2.5 mm (and all values and ranges therebetween).

In another specific configuration, the distance between the two adjacently positioned screw openings is 1.5-4 mm (and all values and ranges therebetween). The two adjacently positioned screw openings can be located at the same distance from the central longitudinal axis of the cervical plate.

In another specific configuration, when the screws are inserted into screw openings 30, the screw opening can be shaped to cause the longitudinal axis of the screw to be at some non-tangential angle relative to top surface of the cervical plate adjacent the particular screw opening. In one non-limiting configuration, the screw openings located nearest to the end of the cervical plate are configured such that the longitudinal axis of the screw when fully placed into the screw opening is oriented ±2-15° (and all values and ranges therebetween) from a right angle to the top surface of the cervical plate (e.g., 75-88° relative to the top surface of the cervical plate). In one non-limiting configuration, the screw openings located in the mid-region of the cervical plate are configured such that the longitudinal axis of the screw when fully placed into the screw opening is oriented ±0-8° (and all values and ranges therebetween) from a right angle to the top surface of the cervical plate (e.g., 82-90° relative to the top surface of the cervical plate). Generally, the screw openings located in the mid-region of the cervical plate are configured differently from the screw openings located nearest to the end of the cervical plate such that the longitudinal axis of the screw when fully placed into the screw opening located in the mid-region of the cervical plate is different from the longitudinal axis of the screw when fully placed into the screw opening located nearest to the end of the cervical plate.

In another specific configuration, the cervical plate can have dual angulation of the screw openings as illustrated in FIGS. 12-16 wherein two or more adjacently positioned screw openings along a longitudinal axis of the cervical plate have a central axis that is not parallel to one another, and two or more pairs of adjacently positioned screw openings along the transverse axis (e.g., axis that is perpendicular to the longitudinal axis) have a central axis that is not parallel to one another. Such an arrangement can be caused by the orientation of the screw openings in the cervical plate and/or by the curvature of the cervical plate along the longitudinal and/or transverse axis of the cervical plate. For example, FIGS. 4, 5, 9, 10, and 13 illustrate a cervical plate that is curved along the longitudinal axis (e.g., 2-4°) and the pair of screw openings at the two ends have a central axis that has an angle (e.g., 9°) that is greater than the angle of curvature of the cervical plate along the longitudinal axis.

In another non-limiting configuration as illustrated in FIG. 16, the central axis of the pair of screw openings centrally located along the longitudinal axis of the cervical plate is generally perpendicular to the top surface of the cervical plate and the two pair of screw openings located at the end portions of the cervical plate have a central axis that is not generally perpendicular to the top surface of the cervical plate.

In another non-limiting configuration as illustrated in FIGS. 14-15, the central axis of the pair of screw openings centrally located along the transverse axis or lateral axis of the cervical plate is generally perpendicular to the top surface of the cervical plate and the two pair of screw openings located at the end portions of the cervical plate have a central axis that is also generally perpendicular to the top surface of the cervical plate. As such, when looking at the central axis of the screw openings along the longitudinal axis of the cervical plate, two or more of the adjacently positioned screw openings have central axis that are non-parallel to one another; and, when looking at the central axis of the screw openings along the transverse axis of the cervical plate, two or more of the adjacently positioned screw openings have central axis that are also non-parallel to one another.

In another specific configuration as illustrated in FIG. 16, the central axis of two or more adjacently positioned screw openings along the longitudinal axis of the cervical plate is such that the bottom portion of the fastener, when fully inserted into the screw opening, angles away from one another; and the central axis of two or more adjacently positioned screw openings along the transverse axis of the cervical plate is such that bottom portion of the fastener, when fully inserted into the screw opening, angle toward one another.

In another specific configuration as illustrated in FIGS. 14-16, the screw openings and the top portion of the fasteners (e.g., screw, etc.) are configured so at least a portion or all of the top of the fastener is flush or slightly recessed in the screw opening when the fastener is fully inserted into the screw opening. Such slightly recessed or flush mounting can be desirable in applications wherein the sharp edges of the fastener are not exposed after the cervical plate is secured to the bone or tissue. In one non-limiting embodiment, the screw opening has a shape that is the same or substantially similar to the top or upper portion of the fastener so the top portion of the fastener is flush with the top surface of the cervical plate that the top portion of the fastener contacts and sits on the screw opening when the fastener is fully inserted into the screw opening.

In another specific configuration as illustrated in FIGS. 1, 2, 17 and 18, a side portion of the cam recess terminates at one or both screw openings located adjacent to the cam recess. The cam recess can optionally include a sloped surface 54 that is located between such screw openings. When a sloped surface exists between the two screw openings, the slope surface is generally configured and oriented so the slope surface does not engage the cam during rotation of the cam in the cam recess. A portion of the can recess includes a cam opening that passes fully through the cervical plate. The diameter of the can openings is generally 2-5 mm (and all values and ranges therebetween). Generally, about 10-50% of the cam recess (and all values and ranges therebetween) does not pass fully through the cervical plate. The cam recess can be configured to include one or more cam stops 56 to limit rotation of a cam in the cam recess. Generally, the cam recess includes one or more cam stops that can a) limit rotation of the cam in a clockwise direction, and/or b) limit rotation of the cam in a counter-clockwise direction. The portion of the cam recess that does not fully penetrate the cervical plate is generally recessed from a top surface of the cervical plate (e.g., recessed about 0.1-0.6 mm and all values and ranges therebetween). The portion of the cam recess that does not fully penetrate the cervical plate has a thickness that is generally 0.2-0.6 mm (and all values and ranges therebetween). The cam recess is generally located 1-3 mm from the outer peripheral edge of the cervical plate.

In another specific configuration, the outer peripheral edge of the cervical plate can include a plurality of undulations on each of the two longitudinal sides of the cervical plate. In one non-limiting arrangement, the angle of curvature of the undulation along the long axis is 6-15° (and all values and ranges therebetween), and the angle of curvature of the undulation along the short axis is 30-40° (and all values and ranges therebetween).

In another specific configuration, the cross-sectional area in the region of a cervical plate at its narrowest width that is formed of a refractory metal alloy (e.g., MoTi alloy) or a metal alloy that includes at least 15 awt. % rhenium and the cross-sectional area is 9-11 mm$^2$ (and all values and ranges therebetween) and the cross-sectional area in the region of the cervical plate at its widest width is 13-15 mm$^2$ (and all values and ranges therebetween). The maximum thickness of the cervical plate at the center of the cervical plate is about 2-3 mm (and all values and ranges therebetween). The minimum width of the cervical plate is about 5-9 mm (and all values and ranges therebetween), and the maximum width of the cervical plate is 14-16.5 mm (and all values and ranges therebetween).

In another specific configuration, the cross-sectional area in the region of a cervical plate at its narrowest width that is formed of a refractory metal alloy (e.g., MoRe alloy) or a metal alloy that includes at least 15 awt. % rhenium and the cross-sectional area is 9-10 mm$^2$ and the cross-sectional area in the region of the cervical plate at its widest width is 11-13 mm$^2$. The maximum thickness of the cervical plate at the center of the cervical plate is about 1-2.5 mm (and all values and ranges therebetween). The minimum width of the cervical plate is about 7-9 mm (and all values and ranges therebetween), and the maximum width of the cervical plate is 14-16.5 mm (and all values and ranges therebetween).

The configuration and dimensions of the cervical plate are novel over prior art cervical plates. These novel dimensions are achievable by forming the cervical plate from a refractory alloy (e.g., MoTi, MoRe, etc.) or a metal alloy that includes at least 15 awt. % rhenium.

The cervical plate and/or fastener system (e.g., screws) can be partially or fully formed of a variety of materials (e.g., titanium, stainless steel, cobalt-chromium, carbon composite, plastic or polymer [e.g., polyetheretherketone (PEEK), polyethylene, ultra-high molecular weight polyethylene (UHMWPE), resorbable polylactic acid (PLA), polyglycolic acid (PGA), etc.], refractory alloys, metal alloy that includes at least 15 awt. % rhenium, etc.

These and other advantages will become apparent to those skilled in the art upon the reading and following of this description.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

To aid the Patent Office and any readers of this application and any resulting patent in interpreting the claims appended hereto, Applicant does not intend any of the appended claims or claim elements to invoke 35 U.S.C. 112(f) unless the words "means for" or "step for" are explicitly used in the particular claim.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall there between. The disclosure has been described with reference to the certain embodiments. These and other modifications of the disclosure will be obvious from the disclosure herein, whereby the foregoing descriptive matter is to be interpreted merely as illustrative of the disclosure and not as a limitation. It is intended to include all such modifications and alterations insofar as they come within the scope of the appended claims.

What is claimed:

1. A bone plate for use as an orthopedic implant comprising a body that includes first and second sets of screw openings and first and second cam recesses; each of said first and second sets of screw openings includes first and second screw openings; said first cam recess is positioned adjacent to said first and second screw openings of said first set of screw openings; said second cam recess is positioned adjacent to said first and second screw openings of said second set of screw openings; each of said first and second cam recesses includes a cam opening that fully penetrates through said bone plate; each of said first and second cam recesses includes a recessed portion that is located about at least a portion of said cam opening and said recessed portion is recessed from a top surface of said body and does not fully penetrate said bone plate and a portion of said recessed portion terminates at a portion of said cam opening at a location that is below said top surface of said body; a top edge of each of said cam openings is located below a top surface of said body; each of said first and second cam recesses includes one or more cam stops to limit rotation of a cam in said respective cam recess; at least a portion of each of said cam stops is recessed below a top surface of said cam recess; said first and second screw openings in said first set of screw openings each have a center that defines a first center axis that runs through said center of said first and second screw openings, and wherein said first cam recess is spaced from said first center axis of said first and second screw openings of said first set of screw openings; said first and second screw openings in said second set of screw openings each have a center that defines a second center axis that runs through said center of said first and second screw openings, and wherein said second cam recess is spaced from said second center axis of said first and second screw openings of said second set of screw openings; a maximum thickness in a region of said body of said bone plate that is widest is greater than a maximum thickness in a region of said body of said bone plate that is narrowest; said body includes a region that extends between at least two cam openings that is absent an opening.

2. The bone plate as defined in claim 1, wherein said cross-sectional area in said region of said body of said bone plate that is widest is 10-40% greater than said cross-sectional area in said region of said body of said bone plate that is narrowest.

3. The bone plate as defined in claim 1, wherein said body is at least partially formed of a refractory alloy or a metal alloy that includes at least 10 awt. % rhenium.

4. The bone plate as defined in claim 1, wherein said bone plate has a maximum width of 10-17 mm, a minimum width of 3-9 mm, a maximum thickness of 0.8-3 mm, a cross-sectional area of 6.0-16 $mm^2$, and wherein said cross-sectional area of said bone plate varies along a longitudinal length of said bone plate.

5. The bone plate as defined in claim 1, wherein a width of each of said screw openings is 2.0-5 mm; each of said screw openings is located 0.7-2.5 mm from an outer peripheral edge of said bone plate.

6. The bone plate as defined in claim 1, wherein a distance of two adjacently positioned screw openings is 0.7-4 mm.

7. The bone plate as defined in claim 1, wherein an angle of a longitudinal central axis of each of first and second screws that is each positioned in one of said screw openings of said first set of screw openings is 0-25° relative to a central longitudinal axis of said screw opening of said first set of screw openings; two or more of said screw openings are configured to cause the angle of the first and second screws that is set in each of said screw openings to be different from one another.

8. The bone plate as defined in claim 1, wherein said each of said first and second cam recesses are configured to releasably engage a cam; a diameter of said cam opening of each of said first and second cam recesses is 2-5 mm; 10-50% of said portion of each of said first and second cam recesses that does not fully penetrate said bone plate is recessed from said top surface of said body at about 0.1-0.6 mm; said portion of each of said first and second cam recesses that does not fully penetrate said bone plate has a thickness of 0.2-0.6 mm; each of said first and second cam recesses is located 1-3 mm from an outer peripheral edge of said bone plate.

9. The bone plate as defined in claim 8, wherein said first cam recess includes a sloped surface positioned between said first and second screw openings of said first set of screw openings that are located adjacent to said first cam recess; said slope surface is configured and oriented so that said slope surface does not engage a cam during rotation of a cam in said first cam recess.

10. The bone plate as defined in claim 1, wherein a portion of first cam recess terminates at said first and second screw openings of said first set of screw openings that is located adjacent to said first cam recess; a portion of a top edge of each of said first and second screw openings of said first set of screw openings is positioned below said top surface of said body.

11. The bone plate as defined in claim 1, wherein said first cam recess includes two of said cam stops; one of said cam stops limits rotation of a cam in a clockwise direction; another of said cam stops limits rotation of a cam in a counter-clockwise direction.

12. The bone plate as defined in claim 1, wherein said bone plate includes one or more undulations on an outer side peripheral edge of said bone plate along a longitudinal axis of said bone plate; an angle of curvature of said undulation along said outer side peripheral edge is 6-40°.

13. The bone plate as defined in claim 1, wherein one or more of said screw openings of said first set of screw openings is configured to enable a plurality of angulations of a screw in said screw opening along a longitudinal axis of the bone plate and along a lateral axis of said bone plate when the screw is positioned and secured in said screw opening.

14. The bone plate as defined in claim 1, wherein one or more of said screw openings of said first set of screw openings includes one or more concavely indented surfaces;

said concavely indented surfaces extend into said screw openings; said concavely indented surfaces are not threaded surfaces.

15. The bone plate as defined in claim 1, wherein said body only includes said first and second cam recesses, and wherein a region that extends between said first and second cam recesses is absent an opening.

16. The bone plate as defined in claim 1, wherein said body further includes a third cam recess; a region that extends between said first and second can cam recesses is absent an opening; a region that extends between said second and third cam recesses includes a body opening and said first and second screw openings of said second set of screw openings; a cross-sectional area of said body opening is less than a cross-sectional area of said cam opening of said first and second cam recesses.

17. The bone plate as defined in claim 16, wherein each of said cam openings of said first, second and third cam recesses includes a central axis that runs through said center of said respective cam opening; said central axis of said cam opening of said first cam recess is spaced forwardly from said first central axis of said first and second screw openings in said first set of screw openings; said central axis of said cam opening of said second cam recess is spaced rearwardly from said second central axis of said first and second screw openings in said second set of screw openings; a spacing between said cam openings of first and second cam recesses is less than a spacing between cam openings of second and third cam recesses.

18. The bone plate as defined in claim 1, wherein each of said cam openings of said first and second cam recesses includes a central axis that runs through said center of said respective cam opening; said central axis of said cam opening of said first cam recess is spaced forwardly from said first central axis of said first and second screw openings in said first set of screw openings; said central axis of said cam opening of said second cam recess is spaced rearwardly from said second central axis of said first and second screw openings in said second set of screw openings.

19. A bone plate for use as a orthopedic implant comprising a body that includes first and second sets of screw openings therethrough; each of said first and second sets of screw openings includes first and second screw openings; a maximum thickness in a region of said body of said bone plate that is widest is greater than a maximum thickness in a region of said body of said bone plate that is narrowest; each of said screw openings is spaced from an outer peripheral edge of said bone plate; an angle of a longitudinal central axis of a screw that is positioned in one of said first and second screw openings of said first and second sets of screw openings is 0-25° relative to a central longitudinal axis; said bone plate includes first and second cam recesses; each of said cam recess is configured to releasably engage a cam; said first cam recess is positioned adjacent to said first set of screw openings and second cam recess is positioned adjacent to said second set screw openings; a portion of each of said first and second cam recesses includes a cam opening that passes fully through said bone plate; each of said first and second cam recesses includes a recessed portion that is located about at least a portion of said cam opening and said recessed portion is recessed from a top surface of said body and does not fully penetrate said bone plate and a portion of said recessed portion terminates at a portion of said cam opening at a location that is below said top surface of said body; a top edge of each of said cam openings is located below a top surface of said body; each of said first and second cam recesses includes one or more cam stops to limit rotation of a cam in said respective cam recess; at least a portion of each of said cam stops is recessed below a top surface of said cam recess; said first and second cam recesses are spaced from said outer peripheral edge of said bone plate; said body includes a region that extends between at least two cam openings that is absent an opening said first and second screw openings in said first set of screw openings each have a center that defines a first center axis that runs through said center of said first and second screw openings, and wherein said first cam recess is spaced from said first center axis; said first and second screw openings in said second set of screw openings each have a center that defines a second center axis that runs through said center of said first and second screw openings, and wherein said second cam recess is spaced from said second center axis; said bone plate includes one or more undulations on said outer side peripheral edge of said bone plate along a longitudinal axis of said bone plate.

20. The bone plate as defined in claim 19, wherein said first and second screw openings in said first set of screw openings are configured to cause said angle of said longitudinal central axis of said screw that is set in each of said first and second screw openings to be different from one another.

21. The bone plate as defined in claim 19, wherein said cross-sectional area in said region of said body of said bone plate that is widest is 10-40% greater than said cross-sectional area in said region of said body of said bone plate that is narrowest.

22. The bone plate as defined in claim 19, wherein said body is at least partially formed of a refractory alloy or a metal alloy that includes at least 10 awt. % rhenium.

23. The bone plate as defined in claim 19, wherein 10-50% of said cam recess does not fully penetrate said bone plate.

24. The bone plate as defined in claim 23, wherein a portion of said first cam recess terminates at at least one screw opening of said first set of screw openings that is located adjacent to said first cam recess.

25. The bone plate as defined in claim 23 wherein said first cam recess includes a sloped surface positioned between said first and second screw openings of said first set of screw openings that are located adjacent to said first cam recess; said slope surface is configured and oriented so that said slope surface does not engage a cam during rotation of a cam in said first cam recess.

26. The bone plate as defined in claim 23, wherein said first cam recess includes two cam stops to limit rotation of a cam in said first cam recess; one of said cam stops limits rotation of a cam in a clockwise direction; another of said cam stops limits rotation of a cam in a counter-clockwise direction.

27. The bone plate as defined in claim 19, wherein one or more of said screw openings of said first set of screw openings is configured to enable a plurality of angulations of a screw in said screw opening along a longitudinal axis of the bone plate and along a lateral axis of said bone plate when the screw is positioned and secured in said screw opening.

28. The bone plate as defined in claim 19, wherein one or more of said screw openings of said first set of screw openings includes one or more concavely indented surfaces; said concavely indented surfaces extend into said one or more screw openings; said concavely indented surfaces are not threaded surfaces.

29. The bone plate as defined in claim 19, wherein said body only includes said first and second cam recesses, and wherein a region that extends between said first and second cam recesses is absent an opening.

30. The bone plate as defined in claim 19, wherein said body further includes a third cam recess; a region that extends between said first and second cam recesses is absent an opening; a region that extends between said second and third cam recesses includes a body opening and said first and second screw openings of said second set of screw openings; a cross-sectional area of said body opening is less than a cross-sectional area of said cam opening of said first and second cam recesses.

31. The bone plate as defined in claim 30, wherein each of said cam openings of said first, second and third cam recesses includes a central axis that runs through said center of said respective cam opening; said central axis of said cam opening of said first cam recess is spaced forwardly from said first central axis of said first and second screw openings in said first set of screw openings; said central axis of said cam opening of said second cam recess is spaced rearwardly from said second central axis of said first and second screw openings in said second set of screw openings; a spacing between said cam openings of first and second cam recesses is less than a spacing between cam openings of second and third cam recesses.

32. The bone plate as defined in claim 19, wherein each of said cam openings of said first and second cam recesses includes a central axis that runs through said center of said respective cam opening; said central axis of said cam opening of said first cam recess is spaced forwardly from said first central axis of said first and second screw openings in said first set of screw openings; said central axis of said cam opening of said second cam recess is spaced rearwardly from said second central axis of said first and second screw openings in said second set of screw openings.

* * * * *